US006875774B2

(12) United States Patent
Kohn et al.

(10) Patent No.: US 6,875,774 B2
(45) Date of Patent: Apr. 5, 2005

(54) AZA-BRIDGED BICYCLIC AMINE DERIVATIVES FOR USE AS NOVEL CHOLINERGIC RECEPTOR LIGANDS

(75) Inventors: Harold Kohn, Chapel Hill, NC (US); T. Kendall Harden, Carrboro, NC (US); Myoung Goo Kim, Chapel Hill, NC (US); Erik Bodor, Durham, NC (US)

(73) Assignee: The University of North Carolina, Chapel Hill, NC (US)

( * ) Notice: Subject to any disclaimer, the term of this patent is extended or adjusted under 35 U.S.C. 154(b) by 0 days.

(21) Appl. No.: 10/213,428

(22) Filed: Aug. 6, 2002

(65) Prior Publication Data

US 2004/0029911 A1 Feb. 12, 2004

(51) Int. Cl.$^7$ .................. C07D 471/08; A61K 31/44
(52) U.S. Cl. .................. 514/299; 546/112; 546/183
(58) Field of Search .................. 546/112, 183; 514/299

(56) References Cited

U.S. PATENT DOCUMENTS

| | | | |
|---|---|---|---|
| 4,870,081 | A | 9/1989 | Orlek et al. |
| 5,397,800 | A | 3/1995 | Alker et al. |
| 5,468,875 | A | 11/1995 | Sabb et al. |
| 5,510,486 | A | 4/1996 | Robinson, III et al. |
| 5,578,602 | A | 11/1996 | Sauerberg et al. |
| 5,658,925 | A | 8/1997 | Miyazawa et al. |
| 6,211,204 | B1 | 4/2001 | Messer et al. |
| 6,211,377 | B1 | 4/2001 | de Schrijver et al. |
| 6,369,081 | B1 | 4/2002 | Rajeswaran et al. |

FOREIGN PATENT DOCUMENTS

| | | | |
|---|---|---|---|
| DE | 4116582 A1 | * | 11/1991 |
| EP | 0 094 742 | | 11/1983 |
| EP | 0 214 772 | | 3/1987 |
| EP | 0 239 321 | | 9/1987 |
| EP | 0 257 741 | | 3/1988 |
| EP | 0 287 356 | | 10/1988 |
| WO | WO 92/07854 | | 5/1992 |
| WO | WO 93/08191 | | 4/1993 |
| WO | WO 95/15073 | * | 8/1993 |

OTHER PUBLICATIONS

King et al, J. Med. Chem. vol. 36, p. 683–689 (1993).*
McElvain et al, JACS, vol.35, p. 2750 (1923).*
Zaitseva et al, Farmakologiya i Toksikologiya (Moscow) vol. 27,No. 6,p. 686–690 (1964).*
King et al., "Substituted Benzamides with Conformationally Restricted Side Chains. 5. Azabicyclo[x,y,z] Derivatives as 5–HT$_4$ Receptor Agonists and Gastric Motility Stimulants" *Journal of Medicinal Chemistry* 36 (6): 683–689 (1993).
Orlek et al., "Comparison of Azabicyclic Esters and Oxidiazoles as Ligands for the Muscarinic Receptor," *Journal of Medicinal Chemistry* 34 (9): 2726–2735 (1991).

Sternbach et al., "Antispasmodics. I: Bicyclic Basic Alcohols", *Journal of the American Chemical Society* 74 2215–2218 (1952).
International Search Report, PCT/US01/21406, Oct. 23, 2002.
Christopoulos et al., *Synthesis and Pharmacological Evaluation of Dimeric Muscarinic Acetylcholine Receptor Agonists*, The Journal of Pharmacology and Experimental Therapeutics, vol. 298, No. 3, 2001, pp. 1260–1968.
Felder et al., *Therapeutic Opportunities for Muscarinic Receptors in the Central Nervous System*, Journal of Medicinal Chemistry, vol. 43, No. 23, Nov. 16, 2000, pp. 4333–4353.
Gohlke et al., *Synthesis and Nicotinic Binding Studies on Enantiopure Diazine Analogues of the Novel (2–Chloro–5–pyridyl)–9–azabicyclo[4.2.1]non–2–ene UB–165*, Journal of Medicinal Chemistry, vol. 45, No. 5, 2002, pp. 1064–1072.
Martell, Jr. et al., *Esters of Bicyclic Aminoalcohols as Potential Anticholinergics III*, Journal of Pharmaceutical Sciences, vol. 52, No. 4, Apr. 1963, pp. 331–336.
McPherson et al., *Structure Elucidation Via Stereoselective Synthesis of the Acetate Center of 1–Azabicyclo[2.2.2] oct–3–yl α–Hydroxy–α–(1–iodo–1–propen–3–yl)–α–phenylacetate (INQP). A High Affinity Muscarinic Imaging Agent for SPECT*, Journal of Organic Chemistry, vol. 61, 1996, pp. 8335–8337.
Portoghese, *Bivalent ligands and the message–address concept in the design of selective opioid receptor antagonists*, Trends Pharmacol. Sci, vol. 10, 1989, pp. 230,235.
Portoghese, *From Models to Molecules: Opioid Receptors Dimers, Bivalent Ligands, and Selective Opioid Receptor Probes*, Journal of Medicinal Chemistry, vol. 44, No. 14, Jul. 5, 2001, pp. 2259–2269.
Rajeswaran et al., *Design, Synthesis, and Biological Characterization of Bivalent 1–Methyl–1,2,5,6–tetrahydropyridyl–1,2,5–thiadiazole Derivatives as Selective Muscarinic Agonists*, Journal of Medicinal Chemistry, vol. 44, No. 26, pp. 4563–4576.
Sternbach et al., *Antispasmodics. II. Esters of Basic Bicyclic Alcohols*, Journal of the American Chemical Society, vol. 74, May 5, 1952, pp. 2219–2221.

(Continued)

*Primary Examiner*—Bernard Dentz
(74) *Attorney, Agent, or Firm*—Myers Bigel Sibley and Sajovec, P.A.

(57) ABSTRACT

The present invention discloses novel cholinergic receptor ligands. The present invention also relates to the synthesis of substituted derivatives of aza-bridged bicyclic amines for use as muscarinic receptor ligands as well as methods of regulating function of certain cholinergic receptors, and hence acting as antagonists, agonists and partial agonists at certain specific cholinergic receptor subtypes. The present invention also relates to methods for treating disorders associated with cholinergic receptors.

28 Claims, 8 Drawing Sheets

OTHER PUBLICATIONS

Sternbach et al., *Antispasmodics. I. Bicyclic Basic Alcohols*, Journal of the American Chemical Society, vol. 74, May 5, 1952, pp. 2215–2218.

Tecle et al., *CI–1017, a functionally $M_1$–selective muscarinic agonist: design, synthesis, and preclinical pharmacology*, Pharmaceutica Acta Helvetiae, vol. 74, 2000, pp. 141–148.

\* cited by examiner

19     20

5

6

Synthesis of Aza-bridged [3.3.1]-Bicyclic Amines

FIG. 8. Key NMR Assignments of 4-9, 12, and 13

4-8     9, 12, 13

| Cpd No. | R | R' | $^1$H NMR[a] | | | | $^{13}$C NMR[b] | | | |
|---|---|---|---|---|---|---|---|---|---|---|
| | | | C(2)HH' | C(8)H | C(8)HH' | C(9)HH' | C(2) | C(7) | C(8) | C(9) |
| 4 | H | H | 3.24 (d, 16.8)<br>3.73 (d, 16.8) | 2.90-2.96 (m) | — | 2.89 (d, 13.0)<br>2.96 (d, 13.0) | 49.5 | 19.1 | 55.2 | 51.4 |
| 5 | CH$_2$OBn | H | 3.33 (d, 16.8)<br>3.89 (d, 16.8) | 3.01-3.02 (m) | 3.52 (dd, 6.5, 9.3)<br>3.65 (dd, 7.5, 9.3) | 2.75 (d, 13.4)<br>3.07 (d, 13.4) | 52.1 | 19.4 | 60.1 | 46.3 |
| 6 | H | CH$_2$OBn | 3.37-3.51 (m) | 3.04-3.13 (m) | 3.37-3.51 (m) | 3.01 (d, 13.2)<br>3.08 (d, 13.2) | 42.5 | 21.7 | 61.5 | 53.2 |
| 7 | CH$_2$N(CH$_3$)$_2$ | H | 3.31 (d, 16.8)<br>3.93 (d, 16.8) | 2.90-2.94 (m) | 2.23 (dd, 6.8, 12.5)<br>2.70 (dd, 8.4, 12.5) | 2.77 (d, 13.6)<br>3.09 (d, 13.6) | 52.5 | 20.9 | 58.8 | 45.9 |
| 8 | H | CH$_2$N(CH$_3$)$_2$ | 3.35 (dd, 1.0, 17.2)<br>3.55 (d, 17.2) | 2.91-2.97 (m) | 2.12 (dd, 7.5, 12.7)<br>2.45 (dd, 6.3, 12.7) | 3.03 (br dt, 1.3, 13.0)<br>3.12 (dt, 2.3, 13.0) | 42.4 | 24.1 | 60.3 | 53.9 |
| 9 | H | H | 3.08-3.23 (m) | 3.08-3.23 (m) | — | 3.29-3.39 (m) | 51.2 | 21.9 | 53.3 | 53.9 |
| 12 | CH$_2$N(CH$_3$)$_2$ | H | 3.27-3.33 (m)<br>3.41-3.50 (m) | 3.08-3.12 (m) | 2.26 (dd, 6.8, 12.4)<br>2.72 (dd, 8.4, 12.4) | 2.91 (d, 13.9)<br>3.32 (d, 13.9) | 53.8 | 23.2 | 56.8 | 48.0 |
| 13 | H | CH$_2$N(CH$_3$)$_2$ | 3.20-3.26 (m)<br>3.34-3.39 (m) | 3.20-3.26 (m) | 2.13-2.34 (m)<br>2.72-2.77 (m) | 3.20-3.26 (m) | 44.6 | 26.2 | 58.1 | 56.0 |

[a]The number in each entry is the chemical shift value (δ) observed in ppm followed by multiplicity of the signal and the coupling constant (s) in Hz. The spectra were recorded at 600 MHz (5, 6), 500 MHz (4, 7, 8, 12, 13) and 300 MHz (9). The solvent used was CDCl$_3$. [b]The number in the entry is the chemical shift value (δ) observed in ppm relative to the solvent peak. The spectra were recorded at 150 MHz (4, 5), 125 MHz (6-8, 12, 13) and 75 MHz (9). The solvent used was CDCl$_3$.

AZA-BRIDGED BICYCLIC AMINE DERIVATIVES FOR USE AS NOVEL CHOLINERGIC RECEPTOR LIGANDS

FIELD OF THE INVENTION

The present invention relates to cholinergic receptor ligands. More particularly, the present invention relates to the synthesis of substituted derivatives of aza-bridged bicyclic amines for use as novel cholinergic receptor ligands, particularly muscarinic and nicotinic receptor ligands. Additionally, the present invention relates to compounds capable of regulating function of certain cholinergic receptors, hence acting as antagonists, agonists or partial agonists at certain cholinergic receptor subtypes. The present invention also relates to methods relevant to the treatment of a wide variety of conditions and disorders, including conditions and disorders associated with dysfunction of the central and autonomic nervous systems.

BACKGROUND OF THE INVENTION

Recent advances have been made in the understanding of the cholinergic nervous system and the receptors therein. These cholinergic receptors are proteins that are embedded in the cell membrane and respond to the chemical acetylcholine. In general there are two types of cholinergic receptors, nicotinic and muscarinic. Each receptor responds to acetylcholine, but they may respond to a different set of agonists and antagonists. Furthermore, cholinoceptive cells with nicotinic and muscarinic receptors may be located in different regions of the nervous system.

Muscarinic and nicotinic receptors mediate a wide variety of physiological responses to the neurotransmitter acetylcholine in the central and peripheral nervous systems. For example, $M_1$ muscarinic receptors play a role in learning and memory function in the brain and regulate gastric acid secretion in the stomach. $M_2$ receptors regulate acetylcholine release in the central nervous system and control cardiac muscle contraction in the heart. $M_3$ receptors help regulate smooth muscle contraction in a variety of tissues and promote secretion from exocrine glands. $M_4$ receptors are thought to play a role in the perception of pain, while $M_5$ receptors are believed to regulate dopaminergic activity in the brain.

Several compounds have been developed synthetically or derived from natural products that bind to muscarinic receptor subtypes. Representative examples from natural products include atropine and scopolamine. As it was found that atropine and scopolamine are both bicyclic amines, several research groups have evaluated other bicyclic amines and their biological activities on cholinergic receptors. Several research groups have also studied and synthesized azabicyclic compounds. See, e.g., Sternbach et al., *J. Am. Chem. Soc.*, "Antispadmodics. Bicyclic Basic Alcohols", 74: 2215–2218 (1952); Sternbach et al., *J. Am. Chem. Soc.*, "Antispadmodics. Esters of Basic Bicyclic Alcohols", 74: 2219–2221 (1952); Martel et al., "Esters of Bicyclic Aminoalcohols as Potential Anticholinergics III", *Journal of Pharmaceutical Sciences*, 52: 331–336 (1963); U.S. Pat. No. 4,870,081, issued to Orlek et al; and U.S. Pat. No. 5,468,875, issued to Sabb et al. Yet, despite the synthesis of these compounds, there still remains a need to find compounds that better regulate the cholinergic receptor.

In addition to the study of bicyclic amines, other references have noted the presence of two pharmacophores within a single muscarinic ligand. A bivalent muscarinic agonist was reported wherein two identical 1,2,5-thiadiazole derivatives were linked to provide a novel series of potent agents. See, e.g., Rajeswaran et al., "Design, Synthesis, and Biological Characterization of Bivalent 1-Methyl-1,2,5,6-tetrahydropyridyl-1,2,5-thiadiazole Derivatives as Selective Muscarinic Agonists", *J. Med. Chem.*, 44, 4563–4576 (2001); Christopoulos et al., "Synthesis and Pharmacological Evaluation of Dimeric Muscarinic Acetylcholine Receptor Agonists", *J. Pharmac. Exp. Therap.*, 298, 1260–1268 (2001). Further research into compounds that may include a dual pharmacophore presence may result in compounds that better regulate cholinergic receptors.

Despite the general knowledge regarding the use of cholinergic receptor subtypes, there are relatively few ligands that selectively or specifically interact with individual muscarinic receptor subtypes. Therefore, it may be advantageous to create new cholinergic receptor ligands that may be able to function as muscarinic or nicotinic receptor ligands.

SUMMARY OF THE INVENTION

The present invention discloses new methods of synthesizing substituted azabicyclic compounds such as a compound as formula I.

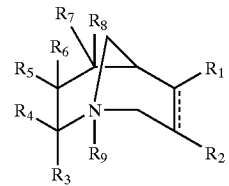

Additionally, the present invention relates pharmaceutical compositions using compounds comprising Formula I above. The present invention also includes methods of treating subjects via the synthesized substituted azabicyclic compounds. The substituted azabicyclic compounds disclosed herein, regulate function of certain cholinergic receptors (i.e., inhibit, increase, etc.), and hence act as antagonists, agonists or partial agonists at certain specific acetylcholine receptor subtypes. The cholinergic receptors include both muscarinic and nicotinic receptors. The present invention also discloses methods for treating a wide variety of conditions and disorders, including conditions and disorders associated with dysfunction of the central and autonomic nervous systems such as cognitive, movement, gastrointestinal and bronchodilation functions necessary for health.

BRIEF DESCRIPTION OF THE DRAWINGS

FIG. 8 depicts NMR assignments of compounds 4–9, 12 and 13.

DETAILED DESCRIPTION OF THE PREFERRED EMBODIMENTS

Figure 1:
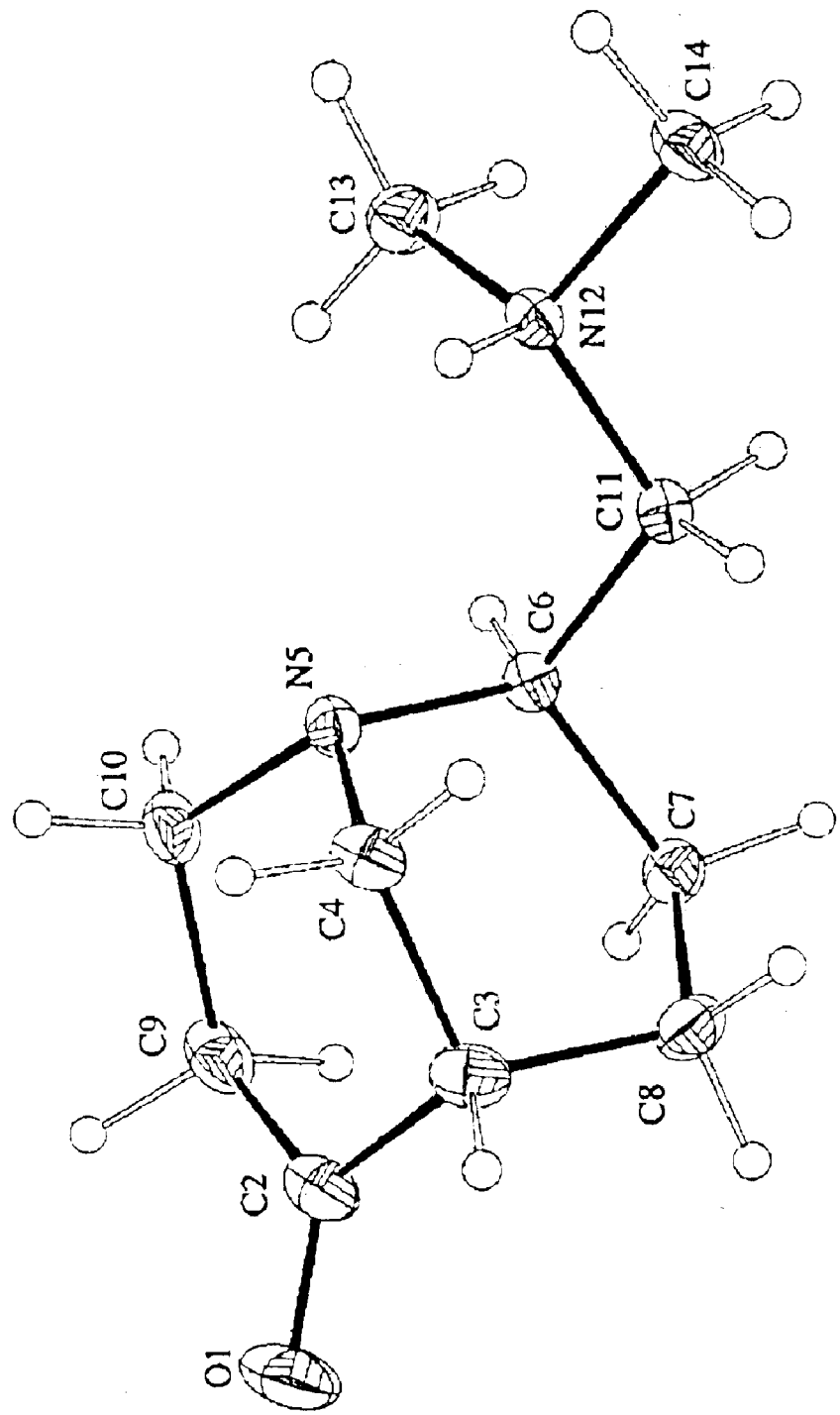
FIG. 1 is an ORTEP X-ray crystallographic diagram of compound 12 indicating that the C(8) dimethylaminomethylene unit is exo to the [3.3.1]-bicyclic ring system.

This invention relates to compounds having pharmaceutical activity, to processes for their preparation and to their use as pharmaceuticals. A group of compounds has now been discovered which may enhance cholinergic function via an action at muscarinic and nicotinic receptors within the central nervous system.

The term "pharmacophore" is known in the art, and, as used herein, refers to a molecular moiety capable of exerting a selected biochemical effect, e.g., inhibition of an enzyme, binding to a receptor, chelation of an ion, and the like. A selected pharmacophore can have more than one biochemical effect, e.g., can be an inhibitor of one receptor (or enzyme) and an antagonist, agonist or partial agonist of a second receptor (or enzyme). A therapeutic agent can include one or more pharmacophores, which can have the same or different biochemical activities.

The term "bivalent ligand" also describes a compound that is not dimeric, as can be broadly defined as a molecule that contains two recognition units linked through a spacer.

The term "antagonist" may be generally defined as a substance that tends to nullify the action of another, i.e., as a drug that binds to a cell receptor without eliciting a biological response.

The term "agonist" is known in the art, and, as used herein, generally refers to a drug that has affinity for and stimulates physiologic activity at cell receptors normally stimulated by naturally occurring substances, thus triggering a biochemical response.

A "partial agonist" may itself cause agonist effects, but because they can displace through competitive action a full agonist from its receptor, the net effect is a reduction in drug effect. As a result, a partial agonist, depending on circumstance, can act as either in agonist or an antagonist.

The compounds of the present invention may include:

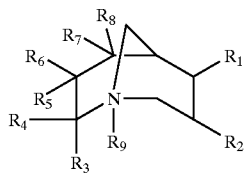

Formula II

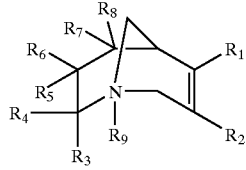

Formula III wherein $R_1$ is selected from the group consisting of alkyl, alkenyl, alkynyl, aryl, acyl, alkylaryl, arylalkyl, oxygen, hydroxy, alkoxy, oxime, amino, hydrazine, nitro, ester and aldehyde, or more preferably $R_1$ is selected from the group consisting of oxygen (O), hydroxy (OH), alkoxy (OR'), amino (NH$_2$, NHR", NR"R'"), hydrazino (NHNH$_2$, N(R")N(R'")H, N(R")N(R")(R'")), and oxime (NOR'). For R', this group may be straight or branched hydrocarbon chain having from C1–6 atoms which is saturated or which is unsaturated and contains double and/or triple bonds, and the hydrocarbon chain may be substituted with a group selected from i) lower alkyl, ii) alkylaryl, iii) substituted aryl. For R', this group may also be aromatic ($C_6$–$C_{14}$) or heterocyclic (e.g., tetrahydrofuranyl, furan, pyrrolidine, pyrrole, piperidine, pyridine). The R' group, regardless of its structure, may have electron withdrawing or electron donating groups, or both. For R" and R'", these groups may be straight or branched hydrocarbon chain having from C1–6 atoms which is saturated or which is unsaturated and contains double and/or triple bonds, and the hydrocarbon chain may be substituted with a group selected from i) lower alkyl, ii) alkylaryl, iii) substituted aryl. For R" and R'", these groups may also be aromatic ($C_6$–$C_{14}$) or heterocyclic (e.g., tetrahydrofuranyl, furan, pyrrolidine, pyrrole, piperidine, pyridine), ester (CO$_2$R'), acyl (C(O)R'). Furthermore it is noted that when $R_1$, is an alkyl in NOR', it may be a straight or branched hydrocarbon chain having from C1–6 atoms which is saturated or which is unsaturated and contains double and/or triple bonds, and hydrocarbon chain may be substituted with a group selected from i) lower alkyl, ii) alkylaryl, iii) substituted aryl. The R, R' and R" groups, regardless of their structure may have electron withdrawing or electron donating groups, or both.

$R_2$ is selected from the group consisting of hydrogen, alkyl, allyl, aryl, alkenyl, alkynyl, alkylaryl, arylalkyl, phenyl, alkenes, alkynes, aryls, halides, alkylhalides, esters, amides, carbonyl, aldehydes and carboxylic acids, with electron withdrawing and/or donating groups, more preferably $R_2$ is selected from the group consisting of hydrogen (H), CO$_2$R$^{iv}$, amides and aryl. When the $R_2$ group is aryl, the group may be C6–14 (e.g., phenyl, naphthyl, anthracenyl) and aromatic heterocycles both five- and six-membered rings (e.g., oxadiazole, oxazole, thiadiazole, thiazole, furan, triazole, tetrazole, pyridine, pyridone, pyrimidine, pyridazine, pyrazine). All of these aromatic and heteroaromatic compounds may have electron withdrawing or electron donating groups, or both. For R$^{iv}$, these groups may be straight or branched hydrocarbon chain having from C1–6 atoms which is saturated or which is unsaturated and contains double and/or triple bonds, and the hydrocarbon chain may be substituted with a group selected from i) lower alkyl, ii) alkylaryl, iii) substituted aryl. For R$^{iv}$, this group may also be aromatic ($C_6$–$C_{14}$) or heterocyclic (e.g., tetrahydrofuranyl, furan, pyrrolidine, pyrrole, piperidine, pyridine).

$R_3$, $R_5$ and $R_7$ are selected from the group consisting of hydrogen, alkyl, allyl, alkenyl, alkynyl alkylaryl, arylalkyl, phenyl, alkenes, alkynes, aryls, amines, alkylhalides, alkyloxyalkyl; alkylthioalkyl; aminoalkyl; alkylaminoalkyl; dialkylaminoalkyl; alkyloxy; alkylthio; halo; amino; alkylamino; dialkylamino; cyclic dialkylamino; amidine, cyclic amidine and their N-alkyl derivatives, with electron withdrawing and/or donating groups, more preferably $R_3$, $R_5$, $R_7$ are selected from the group consisting of hydrogen (H), hydrocarbon or hydrocarbon with heteroatom or heteroatoms ($R'$), $CH_2X$, and X. For $R^v$, this group may be straight or branched hydrocarbon chain having from C1–6 atoms which is saturated or which is unsaturated and contains double and/or triple bonds, and the hydrocarbon chain may be substituted with a group selected from i) lower alkyl, ii) alkylaryl, iii) substituted aryl. For $R^v$, this group may also be aromatic ($C_6$–$C_{14}$) or heterocyclic (e.g., tetrahydrofuranyl, furan, pyrrolidine, pyrrole, piperidine, pyridine). The $R^v$ group, regardless of its structure, may have electron withdrawing or electron donating groups, or both. X may be chosen from OH, $OR^{vi}$, $OC(O)R^{vi}$, $SR^{vi}$, halogen, $OC(O)NHR^{vi}$, $OC(O)NR^{vi}R^{vii}$, $NH_2$, $NHR^{vi}$, $NR^{vi}R^{vii}$, $OC(S)NHR^{vi}$, $OC(S)NR^{vi}R^{vii}$ wherein $R^{vi}$, and $R^{vii}$ may be hydrogen, alkyl, allyl, alkenyl, alkynyl, alkylaryl, arylalkyl, aryl, heteroaryl, heterocycle. The $R^{vi}$ and $R^{vii}$ hydrocarbon chains can be straight or branched hydrocarbon from C1–C6 which is saturated or which is unsaturated and contains double and/or triple bonds and the hydrocarbon chain may be substituted with a select group form i) lower alkyl, ii) alkylaryl, iii) substituted aryl. The $R^{vi}$ and $R^{vii}$ groups, regardless of their structure, may have electron withdrawing or electron donating groups, or both. When $R_3$, $R_5$ and $R_7$ are selected form the group consisting of hydrogen (H), hydrocarbon or hydrocarbon with heteroatom or heteroatoms ($R'$), $CH_2X$, X then $R_4$, $R_6$ and $R_8$ are preferably hydrogen (H), or lower alkyl, unsubstituted or substituted with electron withdrawing or donating groups, or both.

$R_4$, $R_6$ and $R_8$ are selected from the group consisting of hydrogen, alkyl, allyl, alkenyl, alkynyl, alkylaryl, arylalkyl, phenyl, alkenes, alkynes, aryls, amines, halides and alkylhalides, alkoxyalkyl, alkylthioalkyl, aminoalkyl, alkylaminoalkyl, dialkylaminoalkyl, alkoxy, alkylthio, halo, amino, alkylamino, diaalkylamino, cyclic dialkylamino, amidine, cyclic amidine and their N-alkyl derivatives, with electron withdrawing and/or donating groups, more preferably $R_4$, $R_6$ and $R_8$ are selected from the group consisting of hydrogen (H), hydrocarbon or hydrocarbon with heteroatom or heteroatoms ($R'$), $CH_2X$ and X. Again, for $R^v$, this group may be straight or branched hydrocarbon chain having from C1–6 atoms which is saturated or which is unsaturated and contains double and/or triple bonds, and the hydrocarbon chain may be substituted with a group selected from i) lower alkyl, ii) alkylaryl, iii) substituted aryl. For $R^v$, this group may also be aromatic ($C_6$–$C_{14}$) or heterocyclic (e.g., tetrahydrofuranyl, furan, pyrrolidine, pyrrole, piperidine, pyridine). The $R^v$ group, regardless of its structure, may have electron withdrawing or electron donating groups, or both. X may be chosen from OH, $OR^{vi}$, $OC(O)R^{vi}$, $SR^{vi}$, halogen, $OC(O)NHR^{vi}$, $OC(O)NR^{vi}R^{vii}$, $NH_2$, $NHR^{vi}$, $NR^{vi}R^{vii}$, $OC(S)NHR^{vi}$, $OC(S)NR^{vi}R^{vii}$ wherein $R^{vi}$, and $R^{vii}$ may be hydrogen, alkyl allyl, alkenyl, alkynyl, alkylaryl, arylalkyl, aryl, heteroaryl, heterocycle. The $R^{vi}$ and $R^{vii}$ hydrocarbon chains can be straight or branched hydrocarbon from C1–C6 which is saturated or which is unsaturated and contains double and/or triple bonds and the hydrocarbon chain may be substituted with a select group form i) lower alkyl, ii) alkylaryl, iii) substituted aryl. The $R^{vi}$ and $R^{vii}$ groups, regardless of their structure, may have electron withdrawing or electron donating groups, or both. When $R_4$, $R_6$ and $R_8$ are selected from the group consisting of hydrogen (H), hydrocarbon or hydrocarbon with heteroatom or heteroatoms ($R^v$), $CH_2X$, X then $R_3$, $R_5$ and $R_7$ are preferably hydrogen (H), or lower alkyl, unsubstituted or substituted with electron withdrawing or donating groups, or both.

$R_9$ is selected from the group consisting of hydrogen, alkyl, aryl, alkylaryl, arylalkyl, that may be unsubstituted or substituted with electron withdrawing and/or electron donating groups, or both when $R_9$ is one of the above there is an appropriate counterion, preferably, $R_9$ is selected from the group consisting of no substituent, hydrogen (H), alkyl ($R^{vi}$), alkylaryl. When $R_9$ is hydrogen, alkyl, alkylaryl there is an appropriate counterion.

Additionally, any geometric isomer may be formed, i.e., syn or anti, or endo or exo. Preferably the compound will be in an exo isomer or conformation for $R_4$, $R_6$ or $R_8$. Moreover, Formula II and Formula III can exist as their individual enantiomers, racemic forms, enantiomeric mixtures. The compounds of this invention exist as the free bases and pharmaceutically accepted salts.

The present invention also relates to methods for synthesizing certain substituted bicyclic compounds, such as the compounds disclosed above. Additionally, the present invention relates to prodrug derivatives of compounds of the present invention.

Figure 6:
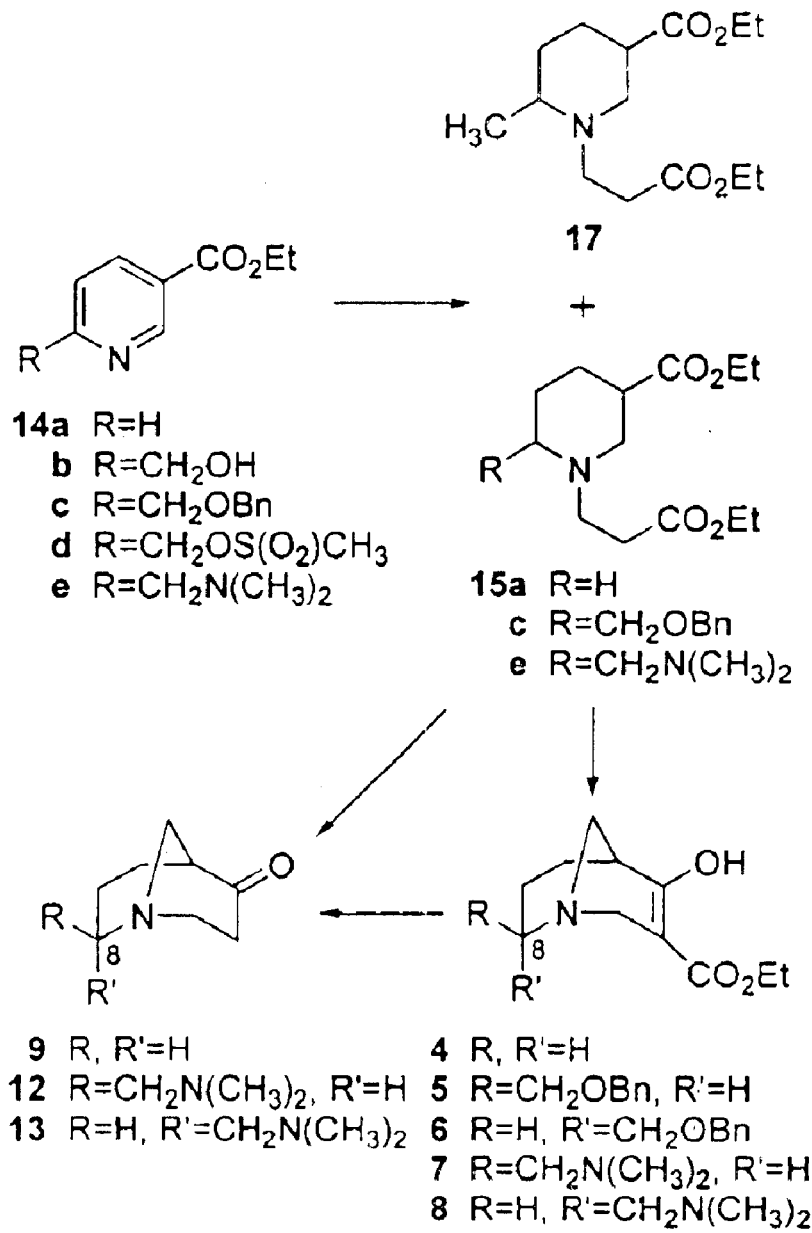
FIG. 6 depicts a general scheme for synthesizing some of the compounds of the present invention.

One of the embodiments of the present invention relates to the synthesis of C(8) substituted 1-azabicyclo[3.3.1] compounds such as nonanes, nonanones, nonanenes, nonyls, nonols, etc. These compounds may be produced by an expedient synthesis which may begin with 2,5-disubstituted pyridines. See FIG. 6. Catalytic reduction of the pyridine to the piperidine followed by treatment with ethyl acrylate and Dieckmann cyclization gave diastereomeric mixtures of C(8) substituted 1-azabicyclo[3.3.1]compounds, which were separable by chromatography. Decarboxylation of the bicyclo[3.3.1]compounds provided the C(8) substituted 1-azabicyclo[3.3.1]nonanones from 1-azabicyclo[3.3.1] nonenes. Structural studies revealed diagonistic $^{13}C$ NMR signals that permit assignment of the orientation of the C(8) substituent.

As stated above, the present invention relates to substituted bicyclic compounds, and most preferably to C(8) substituted azabicyclic compounds. Representative preferred compounds of the present invention include C(8) substituted 3-ethoxycarbonyl-4-hydroxy-1-azabicyclo [3.3.1]non-3-enes, exo-8-benzyloxymethyl-3-ethoxycarbonyl-4-hydroxy-1-azabicyclo[3.3.1]non-3-ene, and C(8) substituted 1-azabicyclo[3.3.1]non-4-ones.

The present invention also may relate to acetylcholine antagonists, agonists and partial agonists, more preferably muscarinic antagonists, agonists and partial agonists. The invention may also relate to methods for providing prevention or treatment of conditions or disorders associated with acetylcholine receptors in a subject susceptible to such a condition or disorder. The present invention also may provide for treatment to a subject suffering from a condition or disorder associated with acetylcholine receptors. For example, the method comprises administering to a patient an amount of a compound effective for providing some degree of prevention of the progression of a disorder such as a CNS disorder, (i.e., provide protective effects), amelioration of the symptoms of the disorder, and/or amelioration of the reoccurrence of the disorder. In particular, the methods of the present invention comprise administering to a patient in need thereof, an amount of a compound selected from the group of compounds of general formula II and general formula III hereinbefore, which amount is effective to prevent or treat the condition or disorder affecting the patient. The present invention further relates to pharmaceutical compositions incorporating the compounds of general formulas II and III above.

The compounds of this invention exist as the free bases and pharmaceutically accepted salts of both the racemic forms, their individual enantiomers, or enantiomeric mixtures. Such enantiomeric mixtures may include 50/50, 60/40, 70/30, 80/20, 90/10, 95/5 and 99/1 mixtures. Additionally, a pure form may be obtained. Both the stereo and optical isomers can be isolated by conventional means or prepared by selective synthesis. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, salicylate, p-toluenesulfonate, and ascorbate; salts with acidic amino acids such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N-dibenzylethylenediamine salt; and salts with basic amino acids such as the lysine salt and arginine salts. The salts may be in some cases be hydrates or organic solvates.

The compounds of the present invention are beneficial in therapeutic applications requiring a selective activation at certain cholinergic receptor subtypes; that is, the compounds are antagonists, agonists and partial agonists at certain cholinergic receptor subtypes, preferably acetylcholine receptor subtypes, and more preferably muscarinic and nicotinic subtypes. The pharmaceutical compositions of the present invention are useful for the prevention and treatment of a wide variety of conditions or disorders. The compounds of the present invention are useful for treating CNS conditions and disorders. The compounds of the present invention may also be useful in treating gastrointestinal disorders.

The pharmaceutical compositions of the present invention may include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder. Although the compounds of this invention are known to act as antagonists of muscarinic receptors, they are also novel templates for the development of related novel compounds that may be agonists or partial agonists at muscarinic or nicotinic receptors.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein by reference in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal for veterinary purposes, (e.g., a mammal such as a horse, mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that may effect the functioning of such systems such as the CNS, the autonomic system (ANS) and other tissues sites involving muscarinic and nicotinic receptors. More specifically, in treating a CNS disorder administration preferably is such so as to optimize the effect upon those relevant receptor subtypes (e.g., those which have an effect upon the functioning of the CNS), while minimizing the effects upon receptor subtypes in muscle and ganglia. Other suitable methods for administering the compounds of the present invention are described in U.S. Pat. No. 5,604,231 to Smith et al., the disclosure of which is incorporated herein by reference in its entirety.

Compounds of the present invention bind to relevant receptors and are antagonists, agonists and partial agonists (i.e., regulate relevant receptor subtypes). Concentrations, determined as the amount of compound per volume of receptor-containing tissue, typically provide a measure of the degree to which that compound binds to and affects relevant receptor subtypes. The compounds of the present invention are selective in that at relevant concentrations (i.e., low concentrations) those compounds bind to, and have regulatory effects upon, receptors associated with the release of neurotransmitters (e.g., dopamine, within the CNS).

The appropriate dose of the compound is that amount effective to prevent occurrence of the symptoms of the condition or disorder, or to treat some symptoms of the condition or disorder from which the patient suffers. By "effective amount", "therapeutic amount" or "effective dose" is meant that amount sufficient to elicit the desired pharmacological or therapeutic effects, thus resulting in effective prevention or treatment of the condition or disorder. Thus, when treating a CNS disorder, an effective amount of compound is an amount sufficient to pass across the blood-brain barrier of the subject, to bind to relevant receptor sites in the brain of the subject, and to regulate relevant muscarinic receptor subtypes (e.g., regulates neurotransmitter secretion, thus resulting in effective prevention or treatment of the disorder). Prevention of the condition or disorder is manifested by delaying the onset of the symptoms of the condition or disorder. Treatment of the condition or disorder is manifested by a decrease in the symptoms associated with the condition or disorder, or an amelioration of the reoccurrence of the symptoms of the condition or disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to regulate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where desired therapeutic effects are observed but below the amounts where muscular effects are observed.

The compounds useful according to the method of the present invention have the ability to bind to, and in most circumstances, regulate muscarinic receptors of the patient (i.e., inhibit, increase, etc.). As such, such compounds have the ability to express muscarinic pharmacology, and in particular, to act as muscarinic antagonists, agonists and partial agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 $\mu$M, often are less than about 100 nM, and frequently are less than about 20 nM.

Compounds of the present invention, when employed in effective amounts in accordance with the method of the present invention, are effective towards providing some degree of prevention of the progression of certain conditions and disorders, amelioration of the symptoms of those conditions and disorders, an amelioration to some degree of the reoccurrence of those conditions and disorders. However, such effective amounts of those compounds are not sufficient to elicit any appreciable side effects, as demonstrated by increased effects relating to the cardiovascular system, and effects to skeletal muscle. As such, administration of certain compounds of the present invention provides a therapeutic window in which treatment of certain conditions and disorders is provided, and side effects are avoided. That is, an effective dose of a compound of the present invention is sufficient to provide the desired effects upon relevant muscarinic receptor subtypes, but is insufficient (i.e., is not at a high enough level) to provide undesirable side effects. Preferably, effective administration of a compound of the present invention resulting in treatment of a wide variety of conditions and disorders occurs upon administration of less than 1/5, and often less than 1/10 that amount sufficient to cause any side effects to a significant degree.

The present invention is primarily concerned with the treatment of human subjects, but the invention also may be carried out on animal subjects, particularly mammalian subjects such as mice, rats, dogs, cats, livestock and horses for veterinary purposes, and for drug screening and drug development purposes.

The present invention also reveals structural elements that may be important for receptor binding. Previous references have shown that muscarinic receptor activity depends on ring size and nitrogen position. The present invention notes that the compounds may include the incorporation of two structurally unique pharmacophores within a single muscarinic ligand. This dual pharmacophore differs from prior references describing bivalent muscarinic agonists where two identical 1,2,5-thiadiazole derivatives were linked to provide a novel series of potent agents. By the term dual pharmacophore, it is meant that the compound has two biological activities that contributes to and enhances the compounds medically useful applications. The compounds of the present invention may include, but are not limited to, two pharmacophores or a single pharmacophore and a non-pharmacophore recognition unit. Alternatively, the compounds of the present invention may also comprise of one pharmacophore.

The following examples are provided to further illustrate the present invention, and should not be construed as limiting thereof.

EXAMPLES

Synthesis

One of the embodiments of the present invention includes the synthesis of C(8) methylene-substituted [3.3.1]-bicyclic amines 4–8. It is known in the art that Dieckmann cyclization of the diethyl ester of 3-carboxypiperidine-1-propionic acid (15a, Scheme 1) provides 4 and that 4 undergoes acid decarboxylation to give 1-azabicyclo[3.3.1]nonan-4-one hydrochloride (9) in 23% overall yield. See, Sternbach et al. "Bicyclic Basic Alcohols", *J. Am. Chem. Soc.*, 1952, 74, 2215–2218. Thus, the present invention may include adopting the Dieckmann route and coupling it with a procedure for the synthesis of 2,5-disubstituted piperidines from the corresponding pyridine (Scheme 1). See, e.g., Bolós et al., "Studies on the Hydrogenation of 6-(Hydroxymethyl) pyridine-2-carboxylates and its Application to the Synthesis of 6-(Hydroxymethyl)piperidine-2-carboxylic Acid Derivatives", *J. Heterocyclic Chem.* 1994, 31, 1493–1496; and Cohen et al., "Facile and General Synthesis of 2-, 3-, or 4-[(Dialkylamino)alkyl]pyridines and -piperidines", *Liebigs Ann. Chem.* 1993, 809–810.

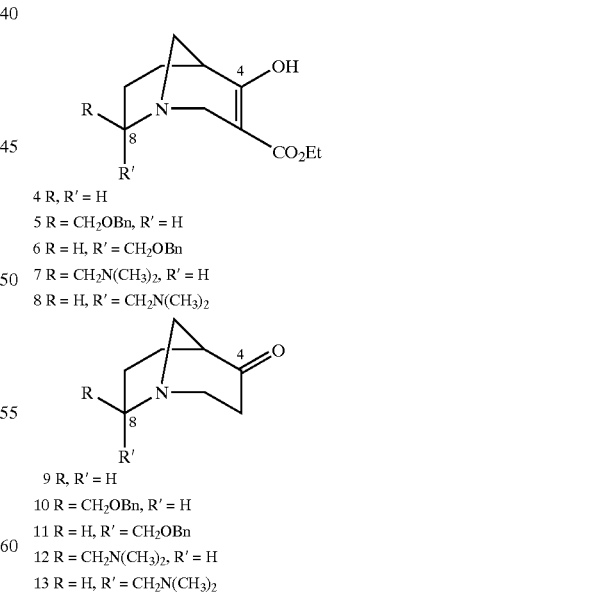

4 R, R' = H
5 R = CH$_2$OBn, R' = H
6 R = H, R' = CH$_2$OBn
7 R = CH$_2$N(CH$_3$)$_2$, R' = H
8 R = H, R' = CH$_2$N(CH$_3$)$_2$

9 R, R' = H
10 R = CH$_2$OBn, R' = H
11 R = H, R' = CH$_2$OBn
12 R = CH$_2$N(CH$_3$)$_2$, R' = H
13 R = H, R' = CH$_2$N(CH$_3$)$_2$

The synthesis of 2,5-disubstituted pyridines 14c–e is generally straightforward. Treatment of 14b (See, Bisel et al., "6-(4-Phenyl-benzyloxy-methyl)guvacine. Synthesis, GABA Uptake Inhibitor and Muscarinic Properties",

*Bioorg. & Med. Chem. Lett.* 1990, 6, 3025–3028) with NaH and benzyl bromide gave ether 14c in 64% yield. Compound 14e was prepared in two steps. First, 14b was converted to mesylate 14d in situ and then the mesylate group was displaced by dimethylamine to give 14e in 82% yield.

Next, a pyridine reductive method such as those reported in the art may be performed. See, e.g., Bolos et al.; Cohen et al; Scopes et al., "New κ-Receptor Agonists Based upon a 2-[(Alkylamino)methyl]piperidine Nucleus", *J. Med. Chem.* 1992, 35, 490–501; Morris et al., "Part VII. The Nature of the Keto-base $C_8H_{13}NO$ from Dioscorine, and an Attempt at its Synthesis", *J. Chem. Soc.* 1963, 1841–1849; and Mauleón et al., "Synthesis and β-Adrenergic Antagonism of 2-(Aryloxy)-1-(2-piperidyl)ethanols", *J. Med. Chem.* 1988, 31, 2122–2126.

For C(2) methylene-substituted pyridines, piperidine formation is accompanied by competitive reduction of the C(2) methylene substituent. The present invention included the examination of several methods and found, for 14c and 14e, that $PtO_2$, $H_2$ and acid provided satisfactory amounts of the desired piperidines. The crude piperidines prepared from 14c and 14e were heated (80° C.) with ethyl acrylate to give the Dieckmann cyclization precursors 15c and 15e, respectively. For the preparation of 15a, ethyl 3-piperidinecarboxylate (16) was used although ethyl nicotinate (14a) could be reduced to create the same product. As expected, a reductive cleavage of the C(2) substituent and pyridine reduction of 14c and 14e was observed, which together gave 17 as a by-product, upon treatment with ethyl acrylate. The catalytic reduction of 14c and 14e proceeded stereoselectively to give 15c and 15e as a single diastereomer after Michael addition with ethyl acrylate while the C(2) methyl piperidine 17 by-product was generated as an approximate 1:1 diastereomeric mixture. This finding suggested that the pyridine C(2) substituent influenced the pathway of reduction.

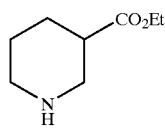

16

Cyclization of 15a, 15c, and 15e proceeded under stringent conditions (tert-BuOK, 110° C., 1 h) to give 4, 5 and 6, and 7 and 8, respectively. Acid decarboxylation (concd. aqueous HCl, 100° C., 14 h) of 4, 7, and 8 gave the corresponding 1-azabicyclo[3.3.1]nonan-4-ones 9, 12, and 13, respectively. Use of these conditions for the preparation of 10 and 11 led to complex product mixtures. Improved yields of 9, 12, and 13 were achieved with the Dieckmann cyclization and acid decarboxylation steps but without characterizing the intermediate esters 4, 7, and 8, respectively.

Structure Analysis

The identities of Dieckmann products 4–8 and the decarboxylated adducts 9, 12 and 13 were determined by IR, $^1$H NMR, $^{13}$C NMR, and mass spectroscopic measurements. The stereochemical orientation of the C(8) substituent was assigned on the basis of the X-ray crystallographic analysis of 12, a comparison of the $^1$H and the $^{13}$C NMR within the data set and the use of diagnostic $^{13}$C NMR patterns for cyclic structures.

FIG. 1 of the present invention shows the ORTEP X-ray crystallographic diagram for 12, indicating that the C(8) dimethylaminomethylene unit is exo to the [3.3.1]bicyclic ring system. Of note, this compound crystallized as the monohydrochloride salt. Structural identification of 12 permitted us to assign the C(8) configuration for the isomeric acid decarboxylated salt 13 as endo and to confidently predict the structures of the corresponding Dieckmann adducts 7 and 8. Further evidence for these assignments came from an assessment of the NMR data set in FIG. 8.

Comparison of the $^1$H and $^{13}$C NMR resonances for 4–9, 12, and 13 revealed distinctive $^{13}$C NMR chemical shift values for the C(2) and C(9) resonances. It was observed that the C(2) chemical shift peak for the exo-adducts 5, 7, and 12 resonated 9.2–10.1 ppm downfield from the C(2) signal in endo-isomers 6, 8, and 13. Correspondingly, the C(9) resonance in 5, 7, and 12 appeared 6.9–8.0 ppm upfield from the same signal in 6, 8, and 13. Similar $^{13}$C NMR chemical shift differences have been reported for the methyl and the C(3) methylene resonances in substituted methylcyclohexanes (See, Stothers, Academic Press, New York: *Carbon-13 NMR Spectroscopy*, 1972, pp. 60–69) and for ring substituents within 2-azabicyclo[3.3.1]nonanes. See, Rubiralta et al., *Structure, Preparation, Reaction and Synthetic Applications of Piperidine and its Derivatives*, Elsevier, Amsterdam, 1991, Chapter 4, pp. 128–129. NOESY experiments on the Dieckmann products 5–8 showed the expected correlations as compared to the proposed $^1$H NMR assignments. For 5, a steric interaction was observed between the C(8) methine hydrogen and the C(2) methylene protons while for the endo-isomer 6 interactions between the C(8) methine hydrogen and the C(9) and C(8)CH$_2$ methylene protons were noted. Similar NOESY correlations were detected for the isomeric pair 7 and 8.

The following steps were used for synthesizing additional azabicyclic analogues. These analogues were then tested to determine if they were able to efficiently bind to cholinergic receptor subtypes.

Synthesis

Ethyl 2-Benzyloxymethyl-5-pyridinecarboxylate (14c). NaH (144 mg, 60% in mineral oil, 3.6 mmol) was slowly added to an anhydrous DMF solution (6 mL) of 14b (543 mg, 3.0 mmol) and BnBr (429 μL, 3.6 mmol) at room temperature, and then the slurry was stirred (30 min) and $H_2O$ (10 mL) was added. The reaction mixture was extracted with EtOAc (3×20 mL) and the combined extracts were dried ($Na_2SO_4$), and concentrated in vacuo. Purification of the concentrated residue by PTLC (EtOAc/hexanes=1/1) gave 14c (520 mg, 64%) as a brown oil: $R_f$ 0.65 (EtOAc/hexanes=1/1); IR (neat) 3031, 2981, 2860, 1721, 1598, 1379, 1281, 1112 cm$^{-1}$; $^1$H NMR (CDCl$_3$) δ 1.40 (t, J=7.2 Hz, 3H), 4.40 (q, J=7.2 Hz, 2H), 4.67 (s, 2H), 4.74 (s, 2H), 7.24–7.42 (m, 5H), 7.59 (d, J=8.1 Hz, 1H), 8.30 (dd, J=1.5, 8.1 Hz, 1H), 9.15 (br s, 1H); $^{13}$C NMR (CDCl$_3$) 14.4, 61.5, 72.9, 73.3, 120.7, 125.1, 127.9, 128.0 (2C), 128.6 (2C), 137.8, 137.9, 150.4, 163.2, 165.4 ppm; MS (+CI) 272 [M+1]$^+$; M$_r$ (+CI) 272.128 97 [M+1]$^+$ (calcd for $C_{16}H_{18}NO_3$ 272.128 67).

Ethyl 2-Dimethylaminomethyl-5-pyridinecarboxylate (14e). Methanesulfonyl chloride (186 μL, 2.4 mmol) was added dropwise to a cooled (0° C.) $CH_2Cl_2$ solution (8 mL) containing 14b (362 mg, 2.0 mmol) and triethylamine (334 μL, 2.4 mmol) under Ar, and then the solution was stirred at 0–5° C. (1 h). $CH_2Cl_2$ (10 mL) was added to the reaction and the organic phase was successively washed with a saturated aqueous NaHCO$_3$ solution (10 mL) and brine (2×10 mL), dried (Na$_2$SO$_4$), filtered and evaporated to give mesylate 14d (508 mg, 98%). Compound 14d was combined with a 2 M dimethylamine THF solution (10 mL, 20 mmol) and triethylamine (279 μL, 2.0 mmol) in EtOH (15 mL) and heated at 80° C. (15 h). The reaction solution was concentrated in vacuo and the residue taken up in $CH_2Cl_2$ (10 mL). The organic solution was washed with $H_2O$ (2×10 mL) and brine (2×10 mL), dried ($Na_2SO_4$), filtered and evaporated. The crude product was purified by PTLC (EtOAc) to give 14e (342 mg, 82%) as a yellow oil: $R_f$ 0.17 (EtOAc/hexanes=3/1); IR (neat) 2976, 2821, 2776, 1723, 1599, 1459, 1376, 1282, 1117 $cm^{-1}$; $^1H$ NMR ($CDCl_3$) δ 1.41 (t, J=7.2 Hz, 3H), 2.31 (s, 6H), 3.65 (s, 2H), 4.41 (q, J=7.2 Hz, 2H), 7.51 (d, J=7.8 Hz, 1H), 8.27 (dd, J=2.1, 7.8 Hz, 1H), 9.16 (d, J=2.1 Hz, 1H); $^{13}C$ NMR ($CDCl_3$) 14.2, 45.5 (2C), 61.2, 65.4, 122.4, 124.7, 137.3, 150.3, 163.5, 165.2 ppm; MS (+CI) 209 $[M+1]^+$; $M_r$ (+CI) 209.129 93 $[M+1]^+$ (calcd for $C_{11}H_{17}N_2O_2$ 209.129 00).

Ethyl 1-[2-(Ethoxycarbonyl)ethyl]-3-piperidinecarboxylate (15a). Ethyl 3-piperidinecarboxylate (3.14 g, 20 mmol) was dissolved in ethyl acrylate (2.50 g, 25 mmol) and stirred at 80° C. (12 h), and then the reaction was concentrated in vacuo, and purified by PTLC (EtOAc/hexanes=3/1) to give 15a (4.64 g, 90%) as a pale yellow oil: $R_f$ 0.51 (EtOAc/hexanes=3/1); IR (neat) 2944, 2806, 1735, 1455, 1376, 1309 $cm^{-1}$; $^1H$ NMR ($CDCl_3$) δ 1.17–1.22 (m, 6H), 1.35–1.51 (m, 2H), 1.62–1.68 (m, 1H), 1.83–1.89 (m, 1H), 1.95–2.02 (m, 1H), 2.11–2.18 (m, 1H), 2.40–2.50 (m, 3H), 2.62–2.70 (m, 3H), 2.91 (dd, J=1.8, 8.1 Hz, 1H), 4.03–4.12 (m, 4H); $^{13}C$ NMR ($CDCl_3$) 14.3 (2C), 24.7, 26.9, 32.5, 41.9, 53.5, 53.9, 55.3, 60.3, 60.4, 172.6, 174.1 ppm; MS (+CI) 258 $[M+1]^+$; $M_r$ (+CI) 258.170 30 $[M+1]^+$ (calcd for $C_{13}H_{24}NO_4$ 258.170 53).

Ethyl 2-Benzyloxymethyl-1-[2-(ethoxycarbonyl)ethyl]-5-piperidinecarboxylate (15c). To an EtOAc solution (0.9 mL) of 14c (271 mg, 1.0 mmol) was added 2 M ethereal HCl (3.6 mL), and then the solvent was removed in vacuo and the residual 14c.HCl salt was dissolved in MeOH (5.4 mL) and $PtO_2$ (14 mg) was added. The mixture was hydrogenated under 1 atm of $H_2$ (1 h). The catalyst was filtered, and the solvent was removed in vacuo. The residue was dissolved in aqueous 1 N NaOH (3.5 mL) and extracted with EtOAc (3×15 mL). The organic extracts were combined, dried ($Na_2SO_4$), concentrated, and then dissolved in ethyl acrylate (1.1 mL, 10 mmol) and stirred at 80° C. (20 h). The reaction was concentrated to dryness and the residue was separated by PTLC (EtOAc/hexanes=2/3) to give 15c (48 mg, 13%) and 17 (32 mg, 12%), respectively. Compound 15c: clear oil; $R_f$ 0.57 (EtOAc/hexanes=1/1); IR (neat) 2978, 2935, 2862, 1731, 1454, 1372, 1181 $cm^{-1}$; $^1H$ NMR ($CDCl_3$) δ 1.24 (t, J=7.2 Hz, 3H), 1.25 (t, J=7.2 Hz, 3H), 1.64–1.77 (m, 4H), 2.43–2.54 (m, 3H), 2.66 (dd, J=3.9, 12.2 Hz, 1H), 2.82–2.97 (m, 4H), 3.45 (dd, J=5.9, 9.6 Hz, 1H), 3.66 (dd, J=5.4, 9.6 Hz, 1H), 4.12 (q, J=7.2 Hz, 4H), 4.47 (1/2 AB, J=12.2 Hz, 1H), 4.52 (1/2 AB, J=12.2 Hz, 1H), 7.27–7.34 (m, 5H), $^{13}C$ NMR ($CDCl_3$) 14.1, 14.2, 23.3, 25.9, 33.1, 40.6, 50.1, 50.3, 57.6, 60.1, 60.2, 69.3, 73.2, 127.4, 127.5 (2C), 128.3 (2C), 138.3, 172.7, 174.1 ppm; MS (+CI) 378 $[M+1]^+$; $M_r$ (+CI) 378.228 63 $[M+1]^+$ (calcd for $C_{21}H_{32}NO_5$ 378.228 05). Compound 17 (King et al., "Substituted Benzamides with Conformationally Restricted Side Chains. 5. Azabicyclo[xyz] Derivatives as 5-$HT_4$ Receptor Agonists and Gastric Motility Stimulants", J. Med. Chem. 1993, 36, 683–689) (cis- and trans-mixture): yellow oil; $R_f$ 0.44 (EtOAc/hexanes=1/1); IR (neat) 2974, 2924, 2814, 1735, 1455, 1377 $cm^{-1}$; $^1H$ NMR ($CDCl_3$) δ 1.00 (d, J=6.6 Hz, 1.4H), 1.10 (d, J=6.6 Hz, 1.6H), 1.23–1.28 (m, 6H), 1.40–2.01 (m, 4H), 2.18–2.31 (m, 1H), 2.42–2.59 (m, 4H), 2.67–2.88 (m, 2H), 3.03–3.10 (m, 1H), 4.08–4.17 (m, 4H), $^{13}C$ NMR ($CDCl_3$) 13.7 (2C), 14.2 (2C), 19.9 (2C), 23.1 (2C), 27.4 (2C), 32.7, 33.8, 41.2, 42.2, 48.8, 49.6, 49.8, 53.3, 54.1, 55.1, 60.2 (2C), 60.3 (2C), 172.8 (2C), 174.1 (2C) ppm; MS (+CI) 272 $[M+1]^+$; $M_r$ (+CI) 272.186 63 $[M+1]^+$ (calcd for $C_{14}H_{26}NO_4$ 272.186 18).

Ethyl 2-Dimethylaminomethyl-1-[2-(ethoxycarbonyl)ethyl]-5-piperidinecarboxylate (15e). Using the same procedure employed for the preparation of 15c and using 14e (335 mg, 1.6 mmol), 2 M ethereal HCl (6 mL), $PtO_2$ (24 mg), and ethyl acrylate (1.7 mL, 16 mmol) gave 15e (259 mg, 51%) and 17 (52 mg, 12%) following PTLC purification (10% MeOH—$CHCl_3$). Compound 15e: reddish yellow oil; $R_f$ 0.37 (10% MeOH—$CHCl_3$); IR (neat) 2945, 2818, 1731, 1457, 1376, 1182 $cm^{-1}$; $^1H$ NMR ($CDCl_3$) δ 1.18 (t, J=7.2 Hz, 3H, $CH_2CH_3$), 1.19 (t, J=7.2 Hz, 3H, $CH_2CH_3$), 1.56–1.70 (m, 4H, C(3)$H_2$, C(4)$H_2$), 2.15 (s, 6H, N($CH_3$)$_2$), 2.26–2.48 (m, 5H, C(5)H, NC$H_2$C$H_2$, ($CH_3$)$_{2NCH2}$), 2.69–2.91 (m, 5H, C(2)H, C(6)$H_2$, NC$H_2$C$H_2$), 4.05 (q, J=7.2 Hz, 2H, C$H_2$C$H_3$), 4.07 (q, J=7.2 Hz, 2H, C$H_2$C$H_3$), the $^1H$ NMR assignments were consistent with the COSY spectrum; $^{13}C$ NMR ($CDCl_3$) 14.0 ($CH_2CH_3$), 14.1 ($CH_2CH_3$), 22.8 (C(3)), 25.5 (C(4)), 33.5 (N$CH_2CH_2$), 40.1 (C(5)), 46.0 (N($CH_3$)$_2$), 49.3 (C(6)), 49.7 (N$CH_2CH_2$), 55.4 (C(2)), 57.7 (($CH_3$)$_2NCH_2$), 60.1 (2C, $CH_2CH_3$), 172.6 (C(O)), 174.2 (C(O)) ppm, the assignments were consistent with the DEPT and HMQC spectra; MS (+CI) 315 $[M+1]^+$; $M_r$ (+CI) 315.229 49 $[M+1]^+$ (calcd for $C_{16}H_{31}N_2O_4$ 315.228 38). Compound 17 (cis- and trans-mixture): $R_f$ 0.75 (10% MeOH—$CHCl_3$); $^1H$ NMR ($CDCl_3$) δ 1.00 (d, J=6.6 Hz, 2H), 1.10 (d, J=6.6 Hz, 1H), 1.21–1.28 (m, 6H), 1.44–2.00 (m, 4H), 2.21–2.30 (m, 1H), 2.42–2.59 (m, 4H), 2.67–2.88 (m, 3H), 4.08–4.17 (m, 4H).

3-Ethoxycarbonyl-4-hydroxy-1-azabicyclo[3.3.1]non-3-ene (4). A suspension of tert-BuOK (505 mg, 4.5 mmol) in anhydrous toluene (4.5 mL) was refluxed (1 h) and then an anhydrous toluene solution (1.5 mL) of 15a (386 mg, 1.5 mmol) was added (20 min) and the reaction mixture was refluxed for an additional 3 h, and then cooled. EtOH (2 mL) was added, and the reaction was filtered (Celite pad) and concentrated in vacuo. The residue was purified by PTLC (5% MeOH—$CHCl_3$) to give 4 (127 mg, 40%) as a yellow oil: $R_f$ 0.21 (5% MeOH—$CHCl_3$); IR (neat) 2932, 2857, 1656, 1292, 1207 $cm^{-1}$; $^1H$ NMR ($CDCl_3$, 500 MHz) δ 1.25 (t, J=7.1 Hz, 3H, $CH_2CH_3$), 1.55–1.64 (m, 2H, C(7)$H_2$), 1.65–1.73 (m, 1H, C(6)HH'), 1.84–1.86 (m, 1H, C(6)HH'), 2.19 (br s, 1H, C(5)H), 2.89 (d, J=13.0 Hz, 1H, C(9)HH'), 2.90–2.96 (m, 2H, C(8)$H_2$), 2.96 (d, J=13.0 Hz, 1H, C(9)HH'), 3.24 (d, J=16.8 Hz, 1H, C(2)HH'), 3.73 (d, J=16.8 Hz, 1H, C(2)HH'), 4.17 (q, J=7.1 Hz, 2H, $CH_2CH_3$), 11.83 (br s, 1H, C(4)OH), the $^1H$ NMR assignments were consistent with the COSY spectrum; $^{13}C$ NMR ($CDCl_3$, 150 MHz) 14.2 ($CH_2CH_3$), 19.1 (C(7)), 26.6 (C(6)), 32.2 (C(5)), 49.5 (C(2)), 51.4 (C(9)), 55.2 (C(8)), 60.2 ($CH_2CH_3$), 99.3 (C(3)), 170.6 (C(O)), 172.1 (C(4) ppm, the assignments were consistent with the DEPT, HMQC and HMBC spectra; MS (+CI) 212 $[M+1]^+$; $M_r$ (+CI) 212.128 08 $[M+1]^+$ (calcd for $C_{11}H_{18}NO_3$ 212.128 67). Anal. ($C_{11}H_{17}NO_3$): C, H, N.

exo-8-Benzyloxymethyl-3-ethoxycarbonyl-4-hydroxy-1-azabicyclo[3.3.1]non-3-ene (5) and endo-8-Benzyloxymethyl-3-ethoxycarbonyl-4-hydroxy-1-azabicyclo[3.3.1]non-3-ene (6). Using the same procedure employed for the preparation of 4 and using tert-BuOK (29 mg, 0.25 mmol) and 15c (32 mg, 0.09 mmol) in anhydrous toluene (1 mL) gave 5 (4.5 mg, 16%) and 6 (4.0 mg, 14%) following PTLC purification (5% MeOH—$CHCl_3$). Compound 5: yellow oil; $R_f$ 0.52 (5% MeOH—$CHCl_3$); IR (neat)

2933, 2863, 1734, 1656, 1370, 1293, 1209 cm$^{-1}$; $^1$H NMR (CDCl$_3$, 600 MHz) δ 1.31 (t, J=7.1 Hz, 3H, CH$_2$CH$_3$), 1.45–1.47 (m, 1H, C(7)HH'), 1.72–1.81 (m, 3H, C(7)HH', C(6)H$_2$), 2.17 (br s, 1H, C(5)H), 2.75 (d, J=13.4 Hz, 1H, C(9)HH'), 3.01–3.02 (m, 1H, C(8)H), 3.07 (d, J=13.4 Hz, 1H, C(9)HH'), 3.33 (d, J=16.8 Hz, 1H, C(2)HH'), 3.52 (dd, J=6.5, 9.3 Hz, 1H), BnOCHH'), 3.65 (dd, J=7.5, 9.3 Hz, 1H, BnOCHH'), 3.89 (d, J=16.8 Hz, 1H, C(2)HH'), 4.23 (q, J=7.1 Hz, 2H, CH$_2$CH$_3$), 4.54 (d, J=12.2 Hz, 1H, PhCHH'O), 4.60 (d, J=12.2 Hz, 1H, PhCHH'O), 7.28–7.35 (m, 5H, Ph), 11.86 (br s, 1H, C(4)OH), the $^1$H NMR assignments were consistent with the COSY and NOESY spectra; $^{13}$C NMR (CDCl$_3$, 150 MHz) 14.2 (CH$_2$CH$_3$), 19.4 (C(7)), 22.7 (C(6)), 31.6 (C(5)), 46.3 (C(9)), 52.1 (C(2)), 60.1 (C(8)), 60.2 (CH$_2$CH$_3$), 70.7 (BnOCH$_2$), 73.1 (PhCH$_2$O), 99.9 (C(3)), 127.0, 127.5 (2C), 127.6 (2C), 138.3 (Ph), 170.9 (C(O)), 171.9 (C(4)) ppm, the assignments were consistent with the DEPT, HMQC and HMBC spectra; MS (+CI) 331 [M]$^+$; M$_r$ (+CI) 331.179 07 [M]$^+$ (calcd for C$_{19}$H$_{25}$NO$_4$ 331.178 36). Anal. (C$_{19}$H$_{25}$NO$_4$): C, H, N. Compound 6: yellow oil; R$_f$ 0.30 (5% MeOH—CHCl$_3$); IR (neat) 2928, 2858, 1657, 1371, 1301, 1209 cm$^{-1}$; $^1$H NMR (CDCl$_3$, 600 MHz) δ 1.22 (t, J=7.1 Hz, 3H, CH$_2$CH$_3$), 1.30–1.40 (m, 2H, C(7)H$_2$), 1.71–1.78 (m, 1H, C(6)HH'), 1.88–1.91 (m, 1H, C(6)HH'), 2.22 (br s, 1H, C(5)H), 3.01 (d, J=13.2 Hz, 1H, C(9)HH'), 3.04–3.13 (m, 1H, C(8)H), 3.08 (d, J=13.2 Hz, 1H, C(9)HH'), 3.37–3.51 (m, 4H, C(2)H$_2$, BnOCH$_2$), 4.06–4.19 (m, 2H, CH$_2$CH$_3$), 4.46 (d, J=12.3 Hz, 1H), PhCHH'O), 4.52 (d, J=12.3 Hz, 1H, PhCHH'O), 7.21–7.28 (m, 5H, Ph), 11.81 (br s, 1H), C(4)OH), the $^1$H NMR assignments were consistent with the COSY and NOESY spectra; $^{13}$C NMR (CDCl$_3$, 125 MHz) 14.3 (CH$_2$CH$_3$), 21.7 (C(7)), 27.6 (C(6)), 32.0 (C(5)), 42.5 (C(2)), 53.2 (C(9)), 60.2 (CH$_2$CH$_3$), 61.5 (C(8)), 71.6 (BnOCH$_2$), 73.1 (PhCH$_2$O), 99.3 (C(3)), 127.6, 127.7 (2C), 128.3 (2C), 138.3 (Ph), 170.7 (C(O)), 172.1 (C(4)) ppm, the assignments were consistent with the DEPT, HMQC and HMBC spectra; MS (+CI) 331 [M]$^+$; M$_r$ (+CI) 331.178 13 [M]$^+$ (calcd for C$_{19}$H$_{25}$NO$_4$ 331.178 36). Anal. C$_{19}$H$_{25}$NO$_4$): C, H, N.

exo-8-Dimethylaminomethyl-3-ethoxycarbonyl-4-hydroxy-1-azabicyclo[3.3.1]non-3-ene (7) and endo-8-Dimethylaminomethyl-3-ethoxycarbonyl-4-hydroxy-1-azabicyclo[3.3.1]non-3-ene (8). Using the same procedure employed for the preparation of 4 and using tert-BuOK (41 mg, 0.4 mmol) and 15e (38 mg, 0.1 mmol) in anhydrous toluene (1.5 mL) gave 7 (4 mg, 12%) and 8 (4 mg, 12%) following PTLC purification (10% MeOH—CHCl$_3$). Compound 7: yellow oil; R$_f$ 0.20 (10% MeOH—CHCl$_3$); IR (neat) 2935, 2862, 2770, 1655, 1456, 1363, 1294, 1208 cm$^{-1}$; $^1$H NMR (CDCl$_3$, 500 MHz) δ 1.32 (t, J=7.2 Hz, 3H, CH$_2$CH$_3$), 1.73–1.83 (m, 4H, C(6)H$_2$, C(7)H$_2$), 2.19 (br s, 1H, C(5)H), 2.23 (dd, J=6.8, 12.5 Hz, 1H, (CH$_3$)$_2$NCHH'), 2.29 (s, 6H, N(CH$_3$)$_2$), 2.70 (dd, J=8.4, 12.5 Hz, 1H), (CH$_3$)$_2$NCHH'), 2.77 (d, J=13.6 Hz, 1H, C(9)HH'), 2.90–2.94 (m, 1H, C(8)H), 3.09 (d, J=13.6 Hz, 1H, C(9) HH'), 3.31 (d, J=16.8 Hz, 1H, C(2)HH'), 3.93 (d, J=16.8 Hz, 1H), C(2)HH'), 4.23 (q, J=7.1 Hz, 2H, CH$_2$CH$_3$), 11.87 (br s, 1H, C(4)OH), the $^1$H NMR assignments were consistent with the COSY and NOESY spectra; $^{13}$C NMR (CDCl$_3$, 125 MHz) 14.7 (CH$_2$CH$_3$), 20.9 (C(7)), 22.9 (C(6)), 32.2 (C(5)), 45.9 (C(9)), 46.1 (2C, N(CH$_3$)$_2$), 52.5 (C(2)), 58.8 (C(8)), 60.7 (CH$_2$CH$_3$), 61.2 ((CH$_3$)$_2$NCH$_2$), 99.2 (C(3)), 171.0 (C(O)), 171.8 (C(4)) ppm, the assignments were consistent with the DEPT, HMQC and HMBC spectra; MS (+CI) 269 [M+1]$^+$; M$_r$ (+CI) 269.185 87 [M+1]$^+$ (calcd for C$_{14}$H$_{25}$N$_2$O$_3$ 269.186 52).

Compound 8: yellow oil; R$_f$ 0.26 (10% MeOH—CHCl$_3$); IR (neat) 2934, 2864, 2773, 1656, 1457, 1366, 1292, 1208 cm$^{-1}$; $^1$H NMR (CDCl$_3$, 500 MHz) δ 1.32 (t, J=7.2 Hz, 3H, CH$_2$CH$_3$), 1.28–1.32 (m, 1H, C(7)HH'), 1.40–1.45 (m, 1H, C(7)HH'), 1.77–1.84 (m, 1H, C(6)HH'), 1.92–1.97 (m, 1H, C(6)HH'), 2.12 (dd, J=7.5, 12.7 Hz, 1H, (CH$_3$)$_2$NCHH'), 2.23 (br s, 1H, C(5)H), 2.27 (s, 6H, N(CH$_3$)$_2$), 2.45 (dd, J=6.3, 12.7 Hz, 1H), (CH$_3$)$_2$NCHH'), 2.91–2.97 (m, 1H, C(8)H), 3.03 (br dt, J=1.3, 13.0 Hz, 1H, C(9)HH'), 3.12 (dt, J=2.3, 13.0 Hz, 1H, C(9)HH'), 3.35 (dd, J=1.0, 17.2 Hz, 1H, C(2)HH'), 3.55 (d, J=17.2 Hz, 1H, C(2)HH'), 4.17–4.30 (m, 2H, CH$_2$CH$_3$), 11.84 (br s, 1H, C(4)OH), the $^1$H NMR assignments were consistent with the COSY and NOESY spectra; $^{13}$C NMR (CDCl$_3$, 125 MHz) 14.7 (CH$_2$CH$_3$), 24.1 (C(7)), 28.4 (C(6)), 32.5 (C(5)), 42.4 (C(2)), 46.6 (2C, N(CH$_3$)$_2$), 53.9 (C(9)), 60.3 (C(8)), 60.7 (CH$_2$CH$_3$), 63.8 ((CH$_3$)$_2$NCH$_2$), 99.3 (C(3)), 170.7 (C(O)), 172.3 (C(4)) ppm, the assignments were consistent with the DEPT, HMQC and HMBC spectra; MS (+CI) 269 [M+1]$^+$; M$_r$ (+CI) 269.185 39 [M+1]$^+$ (calcd for C$_{14}$H$_{25}$N$_2$O$_3$ 269.186 52).

1-Azabicyclo[3.3.1]nonan-4-one (9) from 4. A solution of 4 (21 mg, 0.1 mmol) and concentrated aqueous HCl (1 mL) was refluxed (14 h) and then the solution was basified (30% aqueous KOH) and extracted with CH$_2$Cl$_2$ (5×10 mL). The combined CH$_2$Cl$_2$ extracts were dried (Na$_2$SO$_4$) and concentrated in vacuo to give 9 (5 mg, 38%) as a semi-solid: R$_f$ 0.14 (5% MeOH—CHCl$_3$); IR (neat) 2929, 2857, 1697, 1352, 1201 cm$^{-1}$; $^1$H NMR (CDCl$_3$, 300 MHz) δ 1.64–1.81 (m, 2H, C(7)H$_2$), 1.80–1.86 (m, 2H, C(6)H$_2$), 2.41 (br s, 1H), C(5)H), 2.49–2.54 (m, 2H, C(3)H$_2$), 3.08–3.23 (m, 4H, C(2)H$_2$, C(8)H$_2$), 3.29–3.39 (m, 2H), C(9)H$_2$), the $^1$H NMR assignments were consistent with the COSY spectrum; $^{13}$C NMR (CDCl$_3$, 75 MHz) 21.9 (C(7)), 27.5 (C(6)), 41.8 (C(3)), 45.4 (C(5)), 51.2 (C(2)), 53.3 (C(8)), 53.9 (C(9)), 212.6 (C(4)) ppm, the assignments were consistent with the DEPT and HMQC spectrum; MS (+EI) 139 [M]$^+$; M$_r$ (+EI) 139.100 15 [M]$^+$ (calcd for C$_8$H$_{13}$NO 139.099 71).

1-Azabicyclo[3.3.1]nonan-4-one (9) from 15a. A suspension of tert-BuOK (1.01 g, 9.0 mmol) in anhydrous toluene (12 mL) was refluxed (1 h) and then an anhydrous toluene solution (2.5 mL) of 15a (772 mg, 3.0 mmol) was added (20 min). The reaction mixture was refluxed for an additional 3 h, cooled, and extracted with concentrated aqueous HCl (2×5 mL). The combined aqueous HCl extracts were refluxed (16 h), and then the solution was basified (30% aqueous KOH) and extracted with CH$_2$Cl$_2$ (3×10 mL). The combined CH$_2$Cl$_2$ extracts were dried (Na$_2$SO$_4$) and concentrated in vacuo to give 9 (137 mg, 33%) as a semi-solid: R$_f$ 0.14 (5% MeOH—CHCl$_3$); $^1$H NMR (CDCl$_3$, 300 MHz) δ 1.52–1.82 (m, 2H), 1.90–1.97 (m, 2H), 2.42 (br s, 1H), 2.50–2.55 (m, 2H), 3.10–3.23 (m, 4H), 3.27–3.43 (m, 2H).

exo-8-Dimethylaminomethyl-1-azabicyclo[3.3.1]nonan-4-one-HCl (12) from 7. Employing the procedure for the synthesis of 9 from 4 and using 7 (10 mg, 0.04 mmol) and concentrated aqueous HCl (0.5 mL) gave 12 (3.9 mg, 38%) as a yellow semi-solid following PTLC purification (10% MeOH—CHCl$_3$); R$_f$ 0.08 (10% MeOH—CHCl$_3$); IR (neat) 2932, 2866, 2774, 1700, 1460, 1357, 1277 cm$^{-1}$; $^1$H NMR (CDCl$_3$, 500 MHz) δ 1.52–1.56 (m, 1H, C(7)HH'), 1.72–1.78 (m, 1H, C(6)HH'), 1.80–1.86 (m, 1H, C(7)HH'), 1.97–2.05 (m, 1H, C(6)HH'), 2.26 (dd, J=6.8, 12.4 Hz, 1H, (CH$_3$)$_2$NCHH'), 2.31 (s, 6H, N(CH$_3$)$_2$), 2.39 (br s, 1H, C(5)H), 2.49 (dd, J=6.2, 17.5 Hz, 1H, C(3)HH'), 2.62 (ddd, J=8.9, 10.6, 17.5 Hz, 1H, C(3)HH'), 2.72 (dd, J=8.4, 12.4 Hz, 1H, (CH$_3$)$_2$NCHH'), 2.91 (d, J=13.9 Hz, 1H, C(9)HH'), 3.08–3.12 (m, 1H, C(8)H), 3.27–3.33 (m, 1H, C(2)HH', 3.32 (d, J=13.9 Hz, 1H, C(9)HH'), 3.41–3.50 (m, 1H, C(2)HH'), the ¹H NMR assignments were consistent with the COSY spectrum; ¹³C NMR (CDCl₃, 125 MHz) 23.2 (C(7)), 24.1 (C(6)), 41.1 (C(3)), 45.2 (C(5)), 46.2 (N(CH₃)₂), 48.0 (C(9)), 53.8 (C(2)), 56.8 (C(8)), 62.4 ((CH₃)₂NCH₂), 213.1 (C(4)) ppm, the assignments were consistent with the HMQC and HMBC spectra; MS (+CI) 197 [(M−HCl)+1]⁺; $M_r$ (+CI) 197.165 81 [(M−HCl)+1]⁺ (calcd for $C_{11}H_{21}N_2O$ 197.165 39).

endo-8-Dimethylaminomethyl-1-azabicyclo[3.3.1]nonan-4-one·HCl (13) from 8. Employing the procedure for the synthesis of 9 from 4 and using 8 (12 mg, 0.04 mmol) and concentrated aqueous HCl (0.5 mL) gave 13 (4.3 mg, 42%) as a yellow semi-solid following PTLC purification (10% MeOH—CHCl₃); $R_f$ 0.13 (10% MeOH—CHCl₃); IR (neat) 2936, 2873, 1694, 1462, 1361, 1219 cm⁻¹; ¹H NMR (CDCl₃, 500 MHz) δ 1.29–1.36 (m, 1H, C(7)HH'), 1.57–1.60 (m, 1H, C(7)HH'), 1.89–1.98 (m, 2H, C(6)H₂), 2.13–2.34 (m, 3H, C(3)H₂, (CH₃)₂NCHH'), 2.39 (br s, 1H, C(5)H), 2.45 (s, 6H, N(CH₃)₂), 2.72–2.77 (m, 1H, (CH₃)₂NCHH'), 3.20–3.26 (m, 4H, C(2)HH', C(8)H, C(9)H₂), 3.34–3.39 (m, 1H, C(2)HH'), the ¹H NMR assignments were consistent with the COSY spectrum; ¹³C NMR (CDCl₃, 125 MHz) 26.2 (C(7)), 27.6 (C(6)), 42.0 (C(3)), 44.6 (C(2)), 45.2 (C(5)), 45.8 (N(CH₃)₂), 56.0 (C(9)), 58.1 (C(8)), 62.2 ((CH₃)₂NCH₂), 212.5 (C(4)) ppm, the assignments were consistent with the DEPT, HMQC and HMBC spectra; MS (+CI) 197 [(M−HCl)+1]⁺; $M_r$ (+CI) 197.165 74 [(M−HCl)+1]⁺ (calcd for $C_{11}H_{21}N_2O$ 197.165 39).

exo-8-Dimethylaminomethyl-1-azabicyclo[3.3.1]nonan-4-one·HCl (12) and endo-8-Dimethylaminomethyl-1-azabicyclo[3.3.1]nonan-4-one·HCl (13) from 15e. Employing the procedure for the synthesis of 9 from 15a and using 15e (314 mg, 1.0 mmol), tert-BuOK (337 mg, 3.0 mmol) and anhydrous toluene (6 mL) gave a crude mixture that was heated (85–90° C., 16 h) with concentrated aqueous HCl (4 mL) and then separated by PTLC (25% MeOH—CHCl₃) to give 12 (36 mg, 16%) and 13 (31 mg, 13%), respectively. Compound 12: yellow semi-solid; $R_f$ 0.08 (10% MeOH—CHCl₃); ¹H NMR (CDCl₃, 500 MHz) δ 1.53–1.80 (m, 2H), 1.80–2.01 (m, 2H), 2.26 (dd, J=6.8, 12.4 Hz, 1H), 2.30 (s, 6H), 2.37 (br s, 1H), 2.49 (dd, J=6.2, 17.5 Hz, 1H), 2.62 (ddd, J=8.9, 10.6, 17.5 Hz, 1H), 2.70 (dd, J=8.4, 12.4 Hz, 1H), 2.90 (d, J=13.9 Hz, 1H), 3.05–3.10 (m, 1H), 3.27–3.33 (m, 1H), 3.32 (d, J=13.9 Hz, 1H), 3.40–3.49 (m, 1H).

Compound 13: yellow semi-solid; $R_f$ 0.13 (10% MeOH—CHCl₃); ¹H NMR (CDCl₃, 500 MHz) δ 1.30–1.61 (m, 2H), 1.89–1.98 (m, 2H), 2.10–2.33 (m, 3H), 2.40 (br s, 1H), 2.46 (s, 6H), 2.70–2.75 (m, 1H), 3.21–3.25 (m, 4H), 3.35–3.41 (m, 1H).

X-ray Crystallographic Study of 12. Compound 12 was recrystallized from chloroform-d. Crystals of 12 belong to the space group P2₁/n (monoclinic) with a=10.953 (3) Å; b=7.864 (2) Å; c=25.010 (8) Å; V=2140 Å³, $D_{calcd}$=1.46 Mg.m⁻³, and Z=4. Data were collected at −100° C., and the structure was refined to $R_f$=0.053, $R_w$=0.063 for 5057 reflections with I>3σ(I).

Alternative Route of Synthesis to 5 and 6

Scheme 1

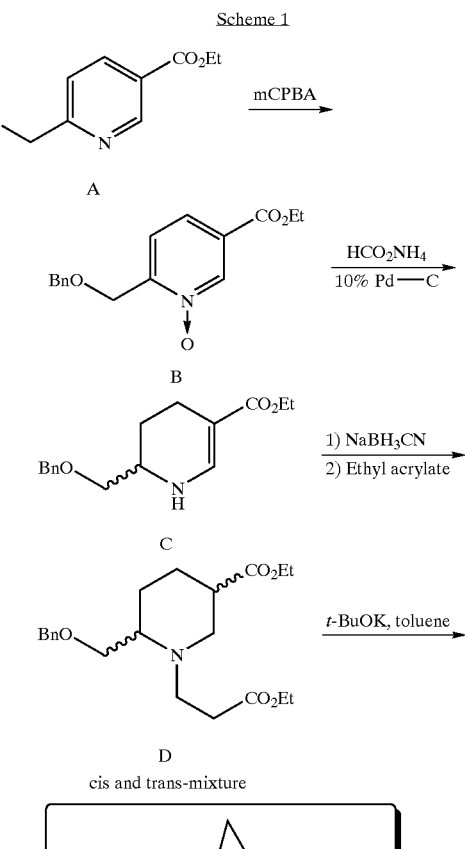

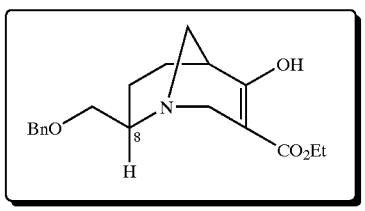

C(8)-exo, racemate Lead Compound 5

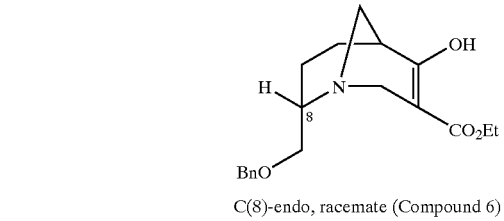

C(8)-endo, racemate (Compound 6)

Ethyl 2-Benzyloxymethyl-5-pyridinecarboxylate N-oxide (B)

A CHCl₃ solution (22 mL) of m-chloroperbenzoic acid (3.72 g, 16.6 mmol) was gradually added to an ice-cooled (0–5° C.), stirred CHCl₃ solution (17 mL) of ethyl 2-benzyloxymethyl-5-pyridinecarboxylate A (4.50 g, 16.6 mmol). The reaction mixture was stirred (4 h), during which the mixture was allowed to come to room temperature. The reaction mixture was successively washed with aqueous 0.5 N NaOH (20 mL), H₂O (20 mL) and the CHCl₃ layer was dried (Na₂SO₄), and concentrated in vacuo. Purification of the concentrated residue by column chromatography (EtOAc/hexanes=3/1) gave N-oxide B (4.00 g, 84%) as yellowish white solid: mp 50–52° C.; $R_f$ 0.19 (EtOAc/hexanes=2/1); IR 3047, 2987, 2859, 1726, 1465, 1386, 1301, 1230, 1118 cm⁻¹; ¹H NMR (CD₃OD, 300 MHz) δ 1.39 (t, J=7.2 Hz, 3H), 4.40 (q, J=7.2 Hz, 2H), 4.73 (s, 2H), 4.77 (s, 2H), 7.27–7.42 (m, 5H), 7.78 (d, J=8.1 Hz, 1H), 8.04 (d, J=8.1 Hz, 1H), 8.71 (s, 1H); $^{13}$C NMR (CD$_3$OD, 75 MHz) 14.4, 63.4, 67.1, 74.7, 125.1, 129.1 (2C), 129.2 (2C), 129.6, 129.9, 130.0, 138.9, 141.0, 155.1, 164.1 ppm; MS (+CI) 288 [M+1]$^+$; M$_r$ (+CI) 288.123 95 [M+1]$^+$ calcd for C$_{16}$H$_{18}$NO$_4$ 288.123 58).

Ethyl (2RS)-2-Benzyloxymethyl-1,2,3,4-tetrahydro-5-pyridinecarboxylate (C)

Dry ammonium formate (9.24 g, 146.5 mmol) was added to a solution of N-oxide B (4.21 g, 14.7 mmol) containing 10% Pd—C (1.45 g) in anhydrous MeOH (130 mL) under an atmosphere of Ar. The reaction mixture was stirred (17 h) at room temperature, and the mixture was filtered. The filtrate was evaporated in vacuo and the residue was triturated with EtOAc (100 mL). The insoluble solid was filtered and the filtrate was concentrated in vacuo. The residue was purified by column chromatography (EtOAc/hexanes=1/2) to give benzyl compound C (3.08 g, 76%) and the corresponding debenzylated compound (271 mg, 10%), respectively.

Benzyl compound C: white solid; mp 64–66° C.; R$_f$ 0.60 (EtOAc/hexanes=2/1); IR (KBr) 3384, 2943, 2857, 1661, 1616, 1490, 1353, 1303, 1207, 1099 cm$^{-1}$; $^1$H NMR (CDCl$_3$, 300 MHz) δ 1.25 (t, J=7.2 Hz, 3H), 1.43–1.55 (m, 1H), 1.76–1.85 (m, 1H), 2.23–2.45 (m, 2H), 3.30–3.57 (m, 3H), 4.13 (q, J=7.2 Hz, 2H), 4.53 (s, 2H), 4.81–4.82 (m, 1H), 7.26–7.40 (m, 5H), 7.46 (d, J=6.0 Hz, 1H); $^{13}$C NMR (CDCl$_3$, 75 MHz) 14.6, 19.6, 23.6, 49.9, 58.9, 73.2, 73.3, 95.9, 127.7, 127.9 (2C), 128.5 (2C), 137.7, 141.9, 168.6 ppm; MS (+CI) 276 [M+1]$^+$; M$_r$ (+CI) 276.160 31 [M+1]$^+$ (calcd for C$_{16}$H$_{22}$NO$_3$ 276.159 97).

Debenzylated compound: colorless oil; R$_f$ 0.16 (EtOAc/hexanes=2/1); IR (neat) 3384, 2940, 2871, 1731, 1660, 1615, 1454, 1369, 1204, 1110 cm$^{-1}$; $^1$H NMR (CDCl$_3$, 300 MHz) δ 1.25 (t, J=7.2 Hz, 3H), 1.44–1.56 (m, 1H), 1.75–1.84 (m, 1H), 2.05–2.42 (m, 2H), 3.34–3.72 (m, 4H), 4.11 (q, J=7.2 Hz, 2H), 5.32–5.34 (m, 1H), 7.50 (d, J=6.0 Hz, 1H); $^{13}$C NMR (CDCl$_3$, 75 MHz) 14.6, 19.5, 23.3, 51.9, 59.0, 65.8, 96.2, 142.1, 168.7 ppm; MS (+CI) 186 [M+1]$^+$; M$_r$ (+CI) 186.113 01 [M+1]$^+$ (calcd for C$_9$H$_{16}$NO$_3$ 186.113 02).

Ethyl 2-Benzyloxymethyl-1-[2-(ethoxycarbonyl)ethyl]-5-piperidinecarboxylate (D)

To a HOAc solution (23 mL) of benzyl compound C (2.62 g, 9.52 mmol) was slowly added a MeOH solution (23 mL) of NaBH$_3$CN (718 mg, 11.42 mmol). The solution was stirred at room temperature (3 h) and concentrated in vacuo. The dried sample (1 h) was treated with ethyl acrylate (10.3 mL, 95.2 mmol), and triethylamine (1.59 mL, 11.4 mmol) at 80–85° C. (17 h). The reaction mixture was concentrated in vacuo and the residue taken up in EtOAc (70 mL). The mixture was washed with H$_2$O (2×50 mL), dried (Na$_2$SO$_4$), filtered, and evaporated. The crude residue was purified by column chromatography (EtOAc/hexanes=1/2) to give the piperidine adduct (3.20 g, 89%, the ratio of cis/trans=1/6) as yellow oil. The piperidine adduct consisted of a mixture of cis- and trans-diastereomers, respectively, that was separable by PTLC (EtOAc/hexanes=1/1).

cis-diastereomer D (0.45 g, 13%): yellow oil; R$_f$ 0.56 (EtOAc/hexanes=1/1); IR (neat) 2978, 2935, 2862, 1731, 1454, 1372, 1181 cm$^{-1}$; $^1$H NMR (CDCl$_3$, 300 MHz) δ 1.24 (t, J=7.2 Hz, 3H), 1.25 (t, J=7.2 Hz, 3H), 1.64–1.77 (m, 4H), 2.43–2.54 (m, 3H), 2.66 (dd, J=3.9, 12.2 Hz, 1H), 2.82–2.97 (m, 4H), 3.45 (dd, J=5.9, 9.6 Hz, 1H), 3.66 (dd, J=5.4, 9.6 Hz, 1H), 4.12 (q, J=7.2 Hz, 4H), 4.47 (1/2 ABq, J=12.2 Hz, 1H), 4.52 (1/2 ABq, J=12.2 Hz, 1H), 7.27–7.34 (m, 5H); $^{13}$C NMR (CDCl$_3$, 75 MHz) 14.1, 14.2, 23.3, 25.9, 33.1, 40.6, 50.1, 50.3, 57.6, 60.1, 60.2, 69.3, 73.2, 127.4, 127.5 (2C), 128.3 (2C), 138.3, 172.7, 174.1 ppm; MS (+CI) 378 [M+1]$^+$; M$_r$ (+CI) 378.228 63 [M+1]$^+$ (calcd for C$_{21}$H$_{32}$NO$_5$ 378.228 05).

trans-diastereomer D (2.75 g, 76%): yellow oil; R$_f$ 0.51 (EtOAc/hexanes=1/1); IR (neat) 2936, 2863, 1730, 1455, 1370, 1183 cm$^{-1}$; $^1$H NMR (CDCl$_3$, 300 MHz) δ 1.24 (t, J=7.2 Hz, 3H), 1.25 (t, J=7.2 Hz, 3H), 1.35–1.50 (m, 2H), 1.69–1.77 (m, 1H), 2.01–2.04 (m, 1H), 2.28–2.58 (m, 5H), 2.83–2.92 (m, 1H), 3.07–3.19 (m, 2H), 3.43 (dd, J=4.2, 9.9 Hz, 1H), 3.52 (dd, J=4.5, 9.9 Hz, 1H), 4.11 (q, J=7.2 Hz, 4H), 4.50 (1/2 ABq, J=12.4 Hz, 1H), 4.54 (1/2 ABq, J=12.4 Hz, 1H), 7.24–7.37 (m, 5H); $^{13}$C NMR (CDCl$_3$, 75 MHz) 14.2 (2C), 26.9, 28.7, 30.6, 41.6, 48.9, 54.1, 59.4, 60.2 (2C), 72.7, 73.3, 127.6, 127.7 (2C), 128.3 (2C), 138.1, 172.7, 174.0 ppm; MS (+CI) 378 [M+1]$^+$; M$_r$ (+CI) 378.229 05 [M+1]$^+$ (calcd for C$_{21}$H$_{32}$NO$_5$ 378.228 05).

exo-8-Benzyloxymethyl-3-ethoxycarbonyl-4-hydroxy-1-azabicyclo[3.3.1]non-3-ene (5) and endo-8-Benzyloxymethyl-3-ethoxycarbonyl-4-hydroxy-1-azabicyclo[3.3.1]non-3-ene (6).

A suspension of tert-BuOK (842 mg, 7.5 mmol) in anhydrous toluene (5 mL) was heated to reflux (1 h) and then an anhydrous toluene solution (1.5 mL) of the cis- and trans-piperidine mixture D (944 mg, 2.5 mmol) was added (20 min) and the reaction mixture was heated to reflux (3 h). The reaction mixture was concentrated in vacuo and the residue taken up in H$_2$O (10 mL) and neutralized (pH 7–8) with concentrated aqueous HCl. The mixture was extracted with CHCl$_3$ (3×20 mL), dried (Na$_2$SO$_4$), filtered and evaporated. The crude mixture was purified by column chromatography (2.5% MeOH/CHCl$_3$) to give exo-compound (297 mg, 36%) and endo-compound (277 mg, 33%) as yellow oils, respectively.

exo compound 5: yellow oil; R$_f$ 0.52 (5% MeOH—CHCl$_3$); $^1$H NMR (CDCl$_3$, 300 MHz) δ 1.29 (t, J=7.2 Hz, 3H), 1.43–1.45 (m, 1H), 1.71–1.81 (m, 3H), 2.16 (br s, 1H), 2.73 (d, J=13.5 Hz, 1H), 2.99–3.02 (m, 1H), 3.05 (d, J=13.5 Hz, 1H), 3.33 (d, J=16.7 Hz, 1H), 3.51 (dd, J=7.5, 9.3 Hz, 1H), 3.64 (dd, J=6.6, 9.3 Hz, 1H), 3.89 (d, J=16.7 Hz, 1H), 4.21 (q, J=7.2 Hz, 2H), 4.52 (d, J=12.3 Hz, 1H), 4.59 (d, J=12.3 Hz, 1H), 7.23–7.34 (m, 5H), 11.89 (br s, 1H); $^{13}$C NMR (CDCl$_3$, 75 MHz) 14.1, 19.2, 22.6, 31.5, 46.1, 52.0, 60.0, 60.1, 70.6, 72.9, 98.8, 127.3, 127.4 (2C), 128.1 (2C), 138.2, 170.7, 171.8 ppm.

endo compound 6: yellow oil; R$_f$ 0.30 (5% MeOH—CHCl$_3$); $^1$H NMR (CDCl$_3$, 300 MHz) δ 1.30 (t, J=7.2 Hz, 3H), 1.31–1.41 (m, 2H), 1.74–1.86 (m, 1H), 1.91–1.98 (m, 1H), 2.23 (br s, 1H), 3.02–3.17 (m, 3H), 3.31–3.57 (m, 4H), 4.12–4.26 (m, 2H), 4.53 (d, J=12.6 Hz, 1H), 4.59 (d, J=12.6 Hz, 1H), 7.27–7.36 (m, 5H), 11.84 (br s, 1H); $^{13}$C NMR (CDCl$_3$, 75 MHz) 14.2, 21.8, 27.6, 32.0, 42.5, 53.3, 60.2, 61.5, 71.9, 73.1, 99.3, 127.5, 127.7 (2C), 128.3 (2C), 138.3, 170.7, 172.2 ppm.

Representative Syntheses for Derivatization at Sites A, B, C, D-1, and D-2 in 5

Scheme 2 shown below illustrates derivation sites that may be created in the azabicylic compounds of the present invention.

1. Derivatization at site A
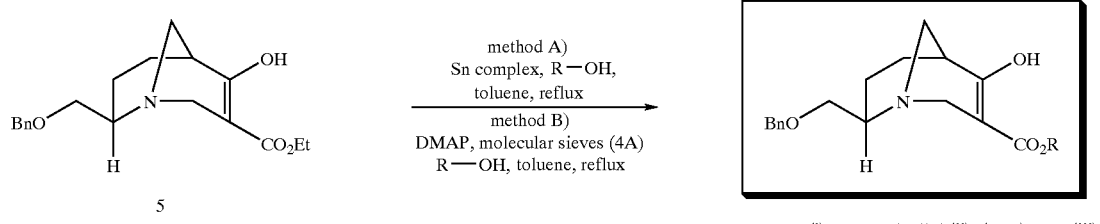
2. Derivatization at site B
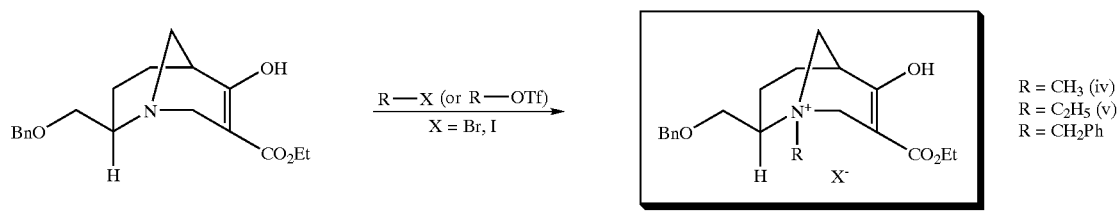
3. Derivatization at site C
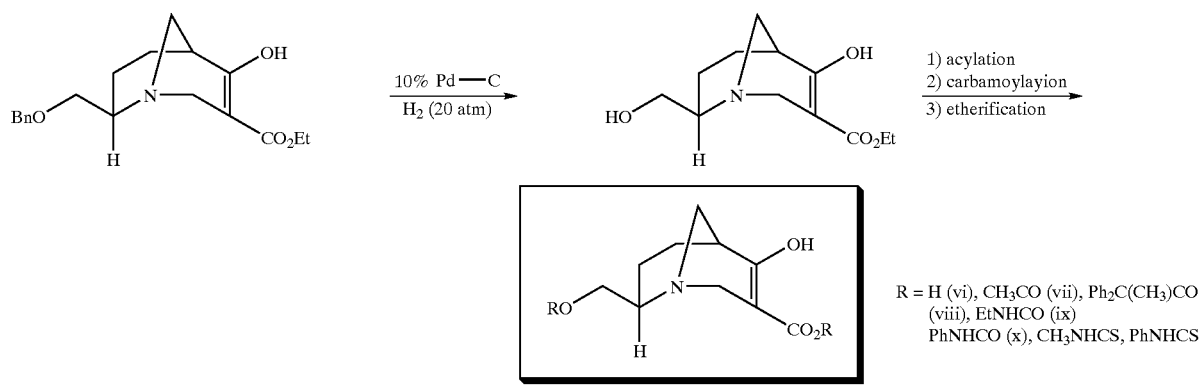
4. Derivatization at site D-1, 2
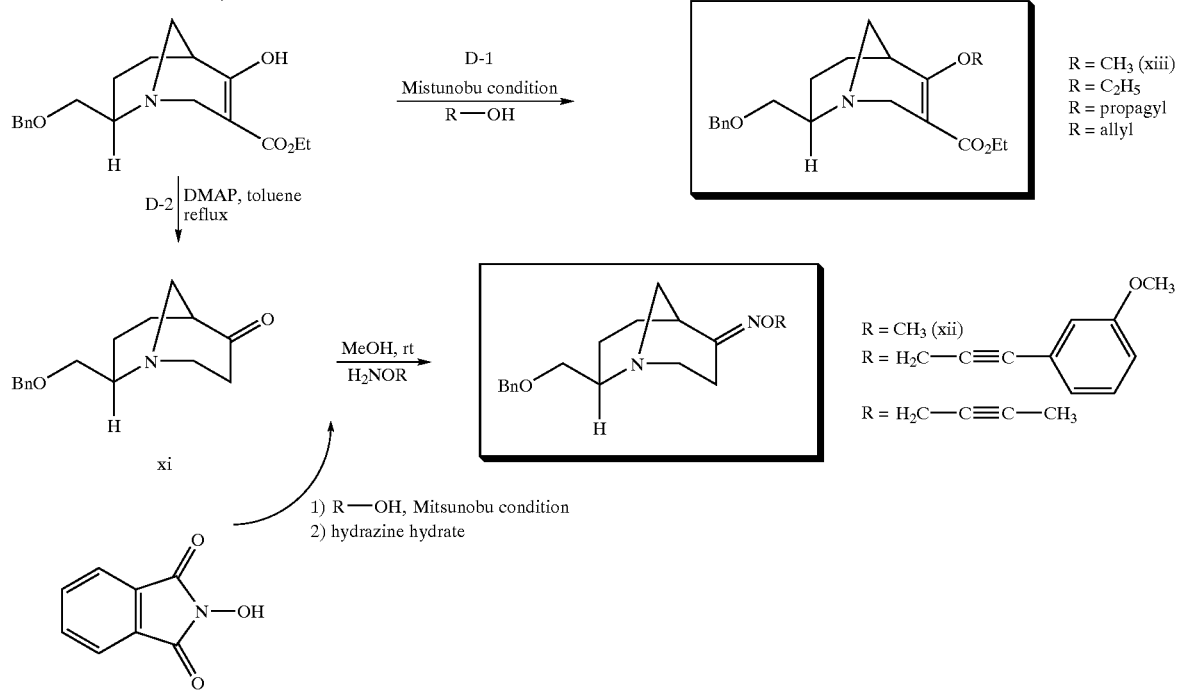

exo-8-Benzyloxymethyl-3-methoxycarbonyl-4-hydroxy-1-azabicyclo [3.3.1]non-3-ene (i)

A mixture of ethyl ester 5 (33 mg, 0.1 mmol), MeOH (61 μL, 1.5 mmol), and 4-(dimethylamino)pyridine (12 mg, 0.1 mmol) was dissolved in anhydrous toluene (4 mL) and then 0.50 g of molecular sieves (4 Å) was added to the vessel. The mixture was refluxed (36 h), cooled to room temperature and then filtered. The filtrate was concentrated in vacuo and the residue was purified by PTLC (2.5% MeOH—CHCl$_3$) to give methyl ester i (30 mg, 96%) as a colorless oil: R$_f$ 0.63 (5% MeOH—CHCl$_3$); $^1$H NMR (CDCl$_3$, 300 MHz) δ 1.44–1.48 (m, 1H), 1.70–1.83 (m, 3H), 2.18 (s, 1H), 2.76 (d, J=13.4 Hz, 1H), 3.01–3.05 (m, 1H), 3.08 (d, J=13.4 Hz, 1H), 3.33 (d, J=16.7 Hz, 1H), 3.52 (dd, J=7.2, 9.3 Hz, 1H), 3.66 (dd, J=6.6, 9.3 Hz, 1H), 3.77 (s, 3H), 3.91 (d, J=16.7 Hz, 1H), 4.53 (d, J=12.3 Hz, 1H), 4.60 (d, J=12.3 Hz, 1H), 7.26–7.35 (m, 5H), 11.80 (s, 1H); $^{13}$C NMR (CDCl$_3$, 75 MHz) 19.4, 22.7, 31.7, 46.3, 51.3, 52.0, 60.4, 70.7, 73.2, 98.6, 127.6, 127.7 (2C), 128.4 (2C), 138.3, 171.1, 171.9 ppm, the assignments were consistent with the DEPT spectrum; MS (+CI) 318 [M+1]$^+$; M$_r$ (+CI) 318.170 84 [M+1]$^+$ (calcd for C$_{18}$H$_{24}$NO$_4$ 318.170 53).

exo-8-Benzyloxymethyl-3-allyloxycarbonyl-4-hydroxy-1-azabicyclo[3.3.1]non-3-ene (ii)

A mixture of ethyl ester 5 (43 mg, 0.13 mmol), allyl alcohol (177 μL, 2.60 mmol), and 4-(dimethylamino) pyridine (16 mg, 0.13 mmol) was dissolved in anhydrous toluene (5 mL) and then 0.65 g of molecular sieves (4 Å) was added to the vessel. The mixture was heated to reflux (40 h), cooled to room temperature and then filtered. The filtrate was concentrated in vacuo and the residue was purified by PTLC (2.5% MeOH—CHCl$_3$) to give allyl ester ii (18 mg, 40%) as an oil: R$_f$ 0.69 (5% MeOH—CHCl$_3$); $^1$H NMR (CDCl$_3$, 300 MHz) δ 1.40–1.49 (m, 1H), 1.70–1.79 (m, 3H), 2.19 (s, 1H), 2.77 (d, J=13.8, Hz, 1H), 2.99–3.03 (m, 1H), 3.08 (d, J=13.8 Hz, 1H), 3.37 (d, J=17.0 Hz, 1H), 3.53 (dd, J=7.5, 9.3 Hz, 1H), 3.66 (dd, J=6.6, 9.3 Hz, 1H), 3.94 (d, J=17.0 Hz, 1H), 4.54 (d, J=12.5 Hz, 1H), 4.60 (d, J=12.5 Hz, 1H), 4.68 (d, J=5.4 Hz, 2H), 5.26 (d, J=10.5 Hz, 1H), 5.34 (d, J=17.4 Hz, 1H), 5.91–6.00 (m, 1H), 7.26–7.36 (m, 5H), 11.78 (s, 1H); $^{13}$C NMR (CDCl$_3$, 75 MHz) 19.5, 22.8, 31.7, 46.3, 52.1, 60.4, 64.7, 70.8, 73.2, 98.8, 118.0, 127.6, 127.7 (2C), 128.4 (2C), 132.0, 138.4, 170.5, 172.4 ppm, the assignments were consistent with the DEPT spectrum.

exo-8-Benzyloxymethyl-3-hexyloxycarbonyl-4-hydroxy-1-azabicyclo[3.3.1]non-3-ene (iii)

An anhydrous toluene solution (2.1 mL) of ethyl ester 5 (43 mg, 0.13 mmol), hexyl alcohol (0.49 mL, 3.90 mmol), and 1-hydroxy-3-chlorotetrabutyldistannoxane (7 mg, 0.013 mmol) was heated to reflux (48 h). The toluene and excess hexyl alcohol were evaporated in vacuo and the residue was purified by PTLC (2.5% MeOH—CHCl$_3$) to give hexyl ester iii (18 mg, 35%) as a brown oil: R$_f$ 0.77 (5% MeOH—CHCl$_3$); $^1$H NMR (CDCl$_3$, 300 MHz) δ 0.90 (t, J=6.6 Hz, 3H), 1.26–1.47 (m, 7H), 1.62–1.82 (m, 5H), 2.18 (s, 1H), 2.76 (d, J=13.5 Hz, 1H), 3.01–3.05 (m, 1H), 3.07 (d, J=13.5 Hz, 1H), 3.33 (d, J=16.8 Hz, 1H), 3.52 (dd, J=7.5, 9.3 Hz, 1H), 3.66 (dd, J=6.9, 9.3 Hz, 1H), 3.91 (d, J=16.8 Hz, 1H), 4.16 (t, J=6.6 Hz, 2H), 4.54 (d, J=12.3 Hz, 1H), 4.61 (d, J=12.3 Hz, 1H), 7.26–7.36 (m, 5H), 11.86 (s, 1H); $^{13}$C NMR (CDCl$_3$, 75 MHz) 14.2, 19.7, 22.7, 23.0, 25.8, 28.8, 31.6, 32.0, 46.6, 52.4, 60.6, 64.6, 71.1, 73.4, 99.3, 127.8, 127.9 (2C), 128.6 (2C), 138.7, 171.2, 172.1 ppm, the assignments were consistent with the DEPT spectrum; MS (+CI) 388 [M+1]$^+$; M$_r$ (+CI) 388.249 07 [M+1]$^+$ (calcd for C$_{23}$H$_{34}$NO$_4$ 388.248 78).

exo-8-Benzyloxymethyl-3-ethoxycarbonyl-4-hydroxy-1-methyl-1-azabicyclo[3.3.1]non-3-ene iodide (iv)

To a diethyl ether solution (1.6 mL) of ethyl ester 5 (33 mg, 0.1 mmol) was added dropwise iodomethane (19 μL, 0.3 mmol). The reaction mixture was stirred at room temperature (30 h) and then the precipitate was filtered, and washed with diethyl ether. The solid was dried to give the quaternary N-methyl compound iv (30 mg, 63%) as a yellow solid: mp 143–146° C.; R$_f$ 0.15 (10% MeOH—CHCl$_3$); $^1$H NMR (DMSO-d$_6$, 300 MHz) δ 1.26 (t, J=7.2 Hz, 3H), 1.60–1.63 (m, 1H), 1.87–2.13 (m, 3H), 2.86 (br s, 1H), 3.23 (s, 3H), 3.30–3.42 (m, 1H), 3.52 (d, J=12.6 Hz, 1H), 3.77–4.34 (m, 7H), 4.55–4.62 (m, 2H), 7.32–7.41 (m, 5H), 11.64 (s, 1H); $^{13}$C NMR (DMSO-d$_6$, 75 MHz) 14.0, 19.8, 21.1, 32.4, 52.6, 55.8, 60.9, 61.3, 68.5, 70.0, 72.2, 94.0, 127.5, 127.6, 127.7, 128.3 (2C), 137.4, 167.5, 168.0 ppm, the assignments were consistent with the DEPT spectrum; MS (+CI) 346 [M–I]$^+$; (–CI) 345 [(M–I)–1]$^+$; M$_r$ (+CI) 346.202 75 [M–I]$^+$ (calcd for C$_{20}$H$_{28}$NO$_4$ 346.201 83).

exo-8-Benzyloxymethyl-3-ethoxycarbonyl-4-hydroxy-1-ethyl-1-azabicyclo[3.3.1]non-3-ene trifluoromethanesulfonate (v)

To a dry CHCl$_3$ solution (1.5 mL) of ethyl ester 5 (33 mg, 0.10 mmol) was added ethyl trifluoromethanesulfonate (16 μL, 0.12 mmol) and the reaction mixture was stirred at room temperature (6 h). The solution was evaporated in vacuo, and the residue was triturated with diethyl ether (10 mL). The precipitate was filtered and dried to give N-ethyl compound v (39 mg, 77%) as a hygroscopic solid: R$_f$ 0.19 (10% MeOH—CHCl$_3$); $^1$H NMR (CDCl$_3$, 300 MHz) δ 1.32 (t, J=7.2 Hz, 3H), 1.41 (t, J=6.6 Hz, 3H), 1.77–1.80 (m, 1H), 1.93–2.21 (m, 3H), 2.80 (s, 1H), 3.21–3.38 (m, 1H), 3.47–3.76 (m, 4H), 3.87–4.29 (m, 6H), 4.54 (d, J=11.7 Hz, 1H), 4.59 (d, J=11.7 Hz, 1H), 7.27–7.35 (m, 5H), 11.99 (s, 1H); $^{13}$C NMR (CDCl$_3$, 75 MHz) 7.5, 13.9, 20.5, 22.4, 33.1, 57.2, 58.7, 61.7 (2C), 67.4, 69.2, 73.7, 93.8, 128.1, 128.3, 128.5, 128.6 (2C), 136.4, 168.2, 168.8 ppm, the assignments were consistent with the DEPT spectrum; MS (+CI) 360 [M–OSO$_2$CF$_3$]$^+$; (–CI) 509 [M]$^+$; M$_r$ (–CI) 509.168 23 [M]$^+$ (calcd for C$_{22}$H$_{30}$NO$_7$F$_3$S 509.169 51).

exo-8-Hydroxymethyl-3-ethoxycarbonyl-4-hydroxy-1-azabicyclo[3.3.1]non-3-ene (vi)

A solution of benzyl compound 5 (320 mg, 0.97 mmol) in CHCl$_3$ (29 mL) and MeOH (3 mL) was hydrogenated over 10% Pd—C (96 mg) under 20 atm of H$_2$ (20 h). The mixture was filtered, and the filtrate was evaporated in vacuo. The residue was purified by column chromatography (10% MeOH—CHCl$_3$) to give hydroxy compound vi (186 mg, 80%) as a oily solid: R$_f$ 0.29 (5% MeOH—CHCl$_3$); $^1$H NMR (CDCl$_3$, 300 MHz) δ 1.12–1.17 (m, 1H), 1.32 (t, J=7.2 Hz, 3H), 1.73–1.89 (m, 3H), 2.23 (s, 1H), 2.71 (d, J=13.4 Hz, 1H), 2.90–2.97 (m, 1H), 3.03 (d, J=13.4 Hz, 1H), 3.21–3.32 (m, 2H), 3.31 (d, J=16.5 Hz, 1H), 3.73 (dd, J=10.5 Hz, 1H), 3.92 (d, J=16.5 Hz, 1H), 4.24 (q, J=7.2 Hz, 2H), 11.90 (s, 1H); $^{13}$C NMR (CDCl$_3$, 75 MHz) 14.2, 19.2, 22.2, 31.5, 44.7, 51.6, 60.0, 60.8, 62.7, 96.9, 170.1, 170.8 ppm, the assignments were consistent with the DEPT spectrum; MS (+CI) 242 [M+1]$^+$; M$_r$ (+CI) 242.138 82 [M+1]$^+$ (calcd for C$_{12}$H$_{20}$NO$_4$ 242.139 23).

exo-8-Acetoxymethyl-3-ethoxycarbonyl-4-hydroxy-1-azabicyclo[3.3.1]non-3-ene (vii)

To a mixture of hydroxy compound vi (30 mg, 0.13 mmol) in CH$_2$Cl$_2$ (3 mL) was successively added triethylamine (19 μL, 0.13 mmol) and acetyl chloride (9 μL, 0.13 mmol). The solution was stirred at room temperature (3 h), and then concentrated to dryness. The residue was purified by PTLC (2.5% MeOH—CHCl$_3$) to give the product vii 22 mg, 62%) as a colorless oil: $R_f$ 0.64 (5% MeOH—CHCl$_3$); $^1$H NMR (CDCl$_3$, 300 MHz) δ 1.30–1.37 (m, 1H), 1.32 (t, J=7.2 Hz, 3H), 1.76–1.86 (m, 3H), 2.09 (s, 3H), 2.22 (s, 1H), 2.78 (d, J=13.7 Hz, 1H), 3.03–3.07 (m, 1H), 3.12 (d, J=13.7 Hz, 1H), 3.32 (d, J=16.5 Hz, 1H), 3.89 (d, J=16.5 Hz, 1H), 4.12–4.33 (m, 4H), 11.88 (s, 1H); $^{13}$C NMR (CDCl$_3$, 75 MHz) 14.2, 19.5, 21.0, 22.7, 31.6, 46.1, 52.1, 59.4, 60.3, 64.5, 99.0, 170.9, 171.0, 171.8 ppm, the assignments were consistent with the DEPT spectrum; MS (+CI) 284 [M+1]$^+$; M$_r$ (+CI) 284.149 91 [M+1]$^+$ (calcd for C$_{14}$H$_{22}$NO$_5$ 284.149 80).

exo-8-(2',2'-Diphenyl)propionoxymethyl-3-ethoxycarbonyl-4-hydroxy-1-azabicyclo[3.3.1]non-3-ene (viii)

To a mixture of hydroxy compound vi (30 mg, 0.13 mmol) in CH$_2$Cl$_2$ (3 mL) was successively added triethylamine (19 μL, 0.13 mmol) and a solution of 2,2-diphenylpropionyl chloride (32 mg, 0.13 mmol) in CH$_2$Cl$_2$ (0.2 mL). The solution was stirred at room temperature (6 h), and then concentrated to dryness. The residue was purified by PTLC (2.5% MeOH—CHCl$_3$) to give the product viii (31 mg, 54%) as a colorless oil: $R_f$ 0.77 (5% MeOH—CHCl$_3$); $^1$H NMR (CDCl$_3$, 300 MHz) δ 1.11–1.23 (m, 1H), 1.31 (t, J=7.2 Hz, 3H), 1.59–1.73 (m, 3H), 1.93 (s, 3H), 2.14 (s, 1H), 2.68 (d, J=13.7 Hz, 1H), 2.95–2.98 (m, 1H), 3.02 (d, J=13.7 Hz, 1H), 3.25 (d, J=16.8 Hz, 1H), 3.81 (d, J=16.8 Hz, 1H), 4.18 (dd, J=7.8 Hz, 1H), 4.22 (q, J=7.2 Hz, 2H), 4.43 (dd, J=6.8 Hz, 10.5 Hz, 1H), 7.21–7.32 (m, 10H), 11.85 (s, 1H); $^{13}$C NMR (CDCl$_3$, 75 MHz) 14.2, 19.0, 22.5, 27.1, 31.5, 46.1, 52.0, 56.6, 59.1, 60.2, 65.3, 98.8, 126.7 (2C), 127.9 (2C), 128.0 (2C), 128.1 (2C), 128.2 (2C), 144.3, 144.4, 170.8, 171.9, 174.8 ppm, the assignments were consistent with the DEPT spectrum; MS (+CI) 450 [M+1]$^+$; M$_r$ (+CI) 450.228 54 [M+1]$^+$ (calcd for C$_{27}$H$_{32}$NO$_5$ 450.228 05).

exo-8-Ethylaminocarbonyloxymethyl-3-ethoxycarbonyl-4-hydroxy-1-azabicyclo[3.3.1]non-3-ene (ix)

To a mixture of hydroxy compound vi (34 mg, 0.14 mmol) in CH$_2$Cl$_2$ (3.4 mL) was added ethyl isocyanate (56 μL, 0.71 mmol). The solution was stirred at room temperature (13 h), and the CH$_2$Cl$_2$ was evaporated in vacuo. The residue was purified by PTLC (5% MeOH—CHCl$_3$) to give the product ix (38 mg, 88%) as a colorless oil: $R_f$ 0.52 (5% MeOH—CHCl$_3$); $^1$H NMR (CDCl$_3$, 300 MHz) δ 1.14 (t, J=7.2 Hz, 3H), 1.21–1.26 (m, 1H), 1.31 (t, J=7.2 Hz, 3H), 1.76–1.84 (m, 3H), 2.22 (s, 1H), 2.78 (d, J=13.5 Hz, 1H), 3.02–3.04 (m, 1H), 3.13–3.27 (m, 3H), 3.32 (d, J=17.0 Hz, 1H), 3.90 (d, J=17.0 Hz, 1H), 4.09–4.19 (m, 2H), 4.23 (q, J=7.2 Hz, 2H), 4.83 (br s, 1H), 11.88 (s, 1H); $^{13}$C NMR (CDCl$_3$, 75 MHz) 14.2, 15.2, 19.4, 22.7, 31.6, 35.9, 45.9, 52.1, 59.8, 60.2, 64.5, 99.0, 156.4, 170.9, 171.8 ppm, the assignments were consistent with the DEPT spectrum; MS (+CI) 313 [M+1]$^+$; M$_r$ (+CI) 313.176 09 [M+1]$^+$ (calcd for C$_{15}$H$_{25}$N$_2$O$_5$ 313.176 35).

exo-8-Phenylaminocarbonyloxymethyl-3-ethoxycarbonyl-4-hydroxy-1-azabicyclo[3.3.1]non-3-ene (x)

To a mixture of hydroxy compound vi (32 mg, 0.13 mmol) in CH$_2$Cl$_2$ (3.2 mL) was added phenyl isocyanate (72 μL, 0.66 mmol). The solution was stirred at room temperature (16 h), and then the CH$_2$Cl$_2$ was evaporated in vacuo. The residue was purified by PTLC (EtOAc/hexanes=3/1) to give the product x (18 mg, 37%) as an oily solid: $R_f$ 0.37 (EtOAc/hexanes=3/1); $^1$H NMR (CDCl$_3$, 300 MHz) δ 1.31 (t, J=7.2 Hz, 3H), 1.36–1.39 (m, 1H), 1.83–1.95 (m, 3H), 2.24 (s, 1H), 2.80 (d, J=13.5 Hz, 1H), 3.03–3.12 (m, 1H), 3.18 (d, J=13.5 Hz, 1H), 3.34 (d, J=16.8 Hz, 1H), 3.92 (d, J=16.8 Hz, 1H), 4.23 (q, J=7.2 Hz, 2H), 4.20–4.27 (m, 1H), 4.38 (dd, J=8.7 Hz, 1H), 6.86 (s, 1H), 7.06 (t, J=7.2 Hz, 1H), 7.27–7.39 (m, 4H), 11.89 (s, 1H); $^{13}$C NMR (CDCl$_3$, 75 MHz) 14.2, 19.5, 22.8, 31.6, 45.7, 52.0, 59.7, 60.3, 64.7, 99.0, 118.6, 123.4 (2C), 129.0 (2C), 137.8, 153.4, 170.8, 171.7 ppm.

exo-8-Benzyloxymethyl-1-azabicyclo[3.3.1]nonan-4-one (xi)

To a toluene solution (18 mL) of ethyl ester 5 (149 mg, 0.45 mmol) was added 4-(dimethylamino)pyridine (58 mg, 0.47 mmol) and then the mixture was heated to reflux (3 d). The solution was concentrated in vacuo and the residue was purified by column chromatography (2.5% MeOH—CHCl$_3$) to give the ketone xi (67 mg, 58%) as a colorless oil: $R_f$ 0.54 (5% MeOH—CHCl$_3$); $^1$H NMR (CDCl$_3$, 300 MHz) δ 1.58–1.83 (m, 3H), 1.93–2.03 (m, 1H), 2.38 (s, 1H), 2.39–2.45 (m, 1H), 2.57–2.69 (m, 1H), 2.84 (d, J=14.1 Hz, 1H), 3.14–3.18 (m, 1H), 3.24–3.40 (m, 3H), 3.51 (dd, J=7.2, 9.5 Hz, 1H), 3.64 (dd, J=6.6 Hz, 9.5 Hz, 1H), 4.55 (d, J=12.3 Hz, 1H), 4.61 (d, J=12.3 Hz, 1H), 7.25–7.38 (m, 5H), $^{13}$C NMR (CDCl$_3$, 75 MHz) 21.3, 23.6, 39.8, 44.5, 48.3, 53.5, 58.1, 71.9, 73.1, 127.5 (3C), 128.3 (2C), 138.2, 212.3 ppm, the assignments were consistent with the DEPT spectrum.

exo-8-Benzyloxymethyl-1-azabicyclo[3.3.1]nonan-4-one, O-Methyloxime (xii)

Ketone xi (29 mg, 0.11 mmol) and O-methoxylamine hydrochloride (10 mg, 0.11 mmol) were dissolved in MeOH (1.5 mL) and then triethylamine (16 μL, 0.11 mmol) was added and the reaction was maintained at room temperature (24 h). The reaction solution was evaporated in vacuo and the residue was purified by PTLC (4% MeOH—CHCl$_3$) to give O-methyloxime (27 mg, 83%) as a 2:1 mixture of E or Z isomers, yellow oil: $R_f$ 0.45, 0.36 (5% MeOH—CHCl$_3$); $^1$H NMR (CDCl$_3$, 300 MHz) δ 1.56–1.67 (m, 2H), 1.75–1.90 (m, 1H), 1.92–2.05 (m, 1H), 2.27–2.43 (m, 2H), 2.56–2.67 (m, 1H), 2.77 (d, J=13.8 Hz, 1H), 2.95–3.25 (m, 4H), 3.45–3.52 (m, 1H), 3.57–3.64 (m, 1H), 3.80 (s, 1H), 3.83 (s, 2H), 4.53 (d, J=12.2 Hz, 1H), 4.60 (d, J=12.2 Hz, 1H), 7.27–7.35 (m, 5H).

exo-8-Benzyloxymethyl-3-ethoxycarbonyl-4-methoxy-1-azabicyclo[3.3.1]non-3-ene (xiii)

Ethyl ester 5 (47 mg, 0.14 mmol), tri-n-butylphosphine (53 μL, 0.21 mmol) and MeOH (9 μL, 0.21 mmol) were dissolved in dry benzene (4.7 mL) and then 1,1'-azobis(N,N-dimethylformamide) (37 mg, 0.21 mmol) was added. The resulting mixture was stirred at room temperature (20 h). The mixture was concentrated in vacuo and then the residue was purified by PTLC (EtOAc/hexanes=3/1) to give product xiii (21 mg, 49%) as an oil: $R_f$ 0.36 (5% MeOH—CHCl$_3$); $^1$H NMR (CDCl$_3$, 300 MHz) δ 1.29 (t, J=7.2 Hz, 3H), 1.40–1.49 (m, 1H), 1.61–1.82 (m, 3H), 2.41 (s, 1H), 2.74 (d, J=13.7 Hz, 1H), 3.02–3.04 (m, 1H), 3.10 (d, J=13.7 Hz, 1H), 3.44 (d, J=17.7 Hz, 1H), 3.52 (dd, J=7.4, 9.5 Hz, 1H), 3.65 (dd, J=6.5, 9.5 Hz, 1H), 3.75 (s, 3H), 3.95 (d, J=17.7 Hz, 1H), 4.19 (q, J=7.2 Hz, 2H), 4.53 (d, J=12.3 Hz, 1H), 4.60 (d, J=12.3 Hz, 1H), 7.27–7.35 (m, 5H); $^{13}$C NMR (CDCl$_3$, 75 MHz) 14.3, 19.0, 22.6, 28.3, 46.9, 54.7, 55.9, 59.8, 60.0, 70.7, 73.1, 108.2, 127.5, 127.6 (2C), 128.3 (2C), 138.4, 163.3, 165.8 ppm, the assignments were consistent with the DEPT spectrum.

Pharmacological Analyses

Figure 2:
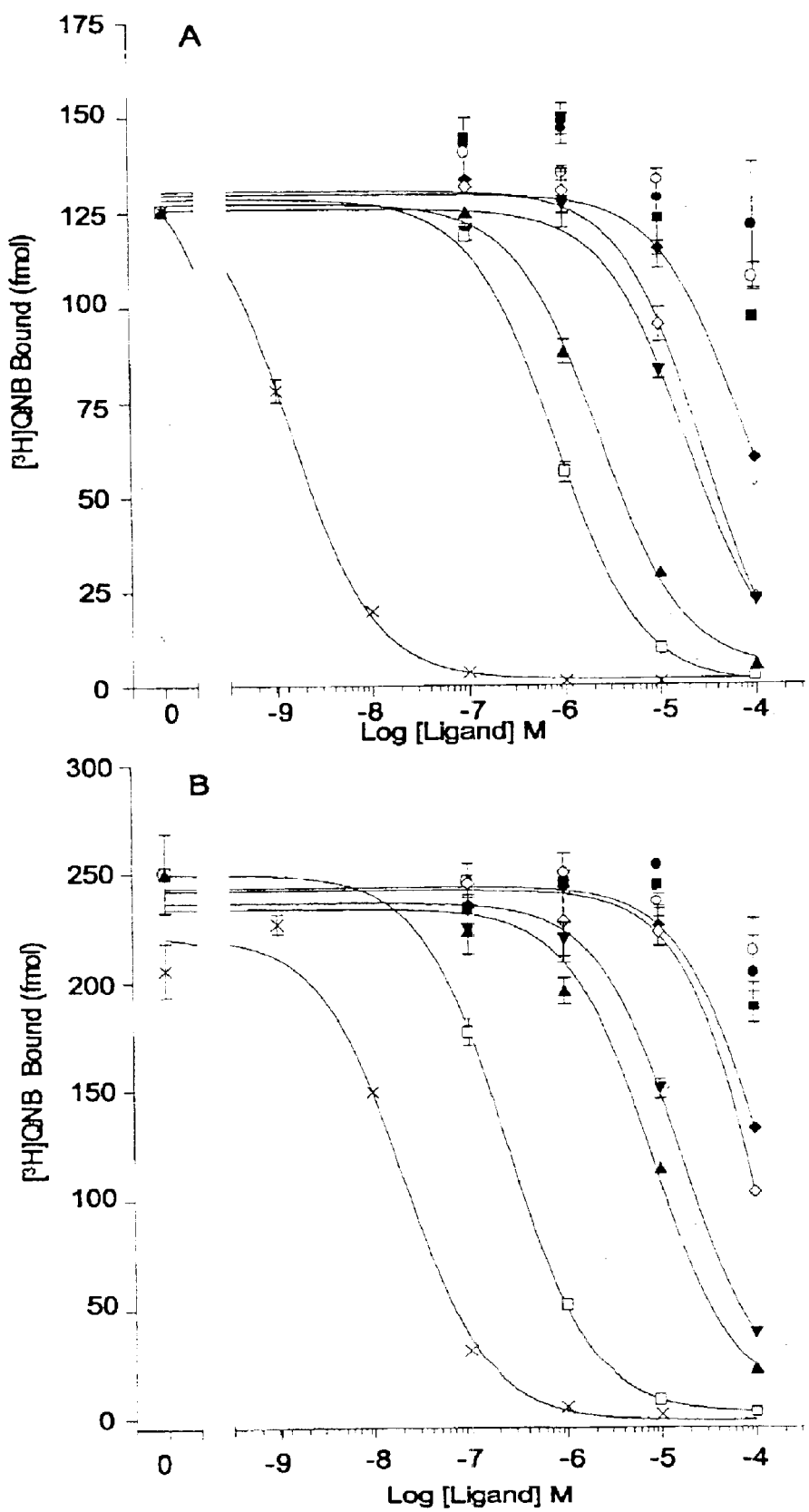
FIG. 2 illustrates a competition binding assay at the human M1 and M2 receptors for ligands 4, 5, 6, 7, 8, 9, 12 and 13.

Muscarinic M1 and M2 Binding Assay. Human M1 and human M2 receptors were expressed in Sf9 insect cells using the baculovirus expression system. Cells were lysed by nitrogen cavitation and membranes were collected through differential centrifugation and resuspended in a buffer containing 20 mM HEPES, pH 8, 250 mM sucrose, 0.1 mM EDTA and a protease inhibitor cocktail for a final protein concentration of 5–10 mg/mL. Competition binding assays were performed essentially as described in a volume of 2 mL using 10 µL membrane (50–100 µg of protein), 200 pM [$^3$H]QNB (approx. 20,000 cpm/assay) and various concentrations of competing drugs (1 or compounds 4–9, 12 or 13) in binding buffer (20 mM HEPES, pH 7.5, 150 mM NaCl, 3 mM MgCl$_2$, 1 mM EDTA). See FIG. 2. Incubations were for 90 min at 30° C. The assays were terminated by addition of 4 mL of wash buffer (20 mM Tris, pH 7.5, 150 mM NaCl, 2 mM MgCl$_2$), quick filtration over Whatman GF/A filters, and two washes with 4 mL of wash buffer. The filters were placed into scintillation vials with 5 mL of scintillation fluid and radioactivity quantitated. FIG. 2 depicts a competition binding assay at the human M1 and M2 receptors: Increasing amounts of the indicated analogue were incubated with [$^3$H]QNB and membranes expressing either the M1 (A) or M2 (B) muscarinic receptor. The data shown include atropine marked as (×), and compounds 4 (▲), 5 (□), 6 (▼), 7 (◇), 8 (♦), 9 (○), 12 (●), and 13 (■) marked accordingly. The data shown are representative of three independent experiments performed in duplicate for both M1 and M2 receptors.

Table 1 show below illustrates the binding Affinities of compounds 4–9, 12 and 13 to human muscarinic receptors.

TABLE 1

| Compound No. | hM1 receptor Ki[a] | hM2 receptor Ki[a] |
|---|---|---|
| 4 | 1008 ± 68 nM | 2850 ± 179 nM |
| 5 | 202.5 ± 83 nM | 84.3 ± 8.1 nM |
| 6 | 10333 ± 2375 nM | 7347 ± 1092 nM |
| 7 | 16810 ± 15190 nM[b] | 23900 ± 13670 nM |
| 8 | 12430 ± 3744 nM | 47570 ± 14790 nM |
| 9 | >100 µM[c] | >100 µM[c] |
| 12 | >100 µM[c] | >100 µM[c] |
| 13 | >100 µM[c] | >100 µM[c] |
| Atropine (1) | 0.43 ± 0.1 nM | 6.00 ± 1.1 nM |

[a]Ki values were calculated according to the formula $$Ki = \frac{IC_{50}}{1 + \frac{[[^3H]QNB]}{K_D}}$$

where IC$_{50}$ is the concentration of competing analogue that inhibited [$^3$H]QNB binding by 50%, [[$^3$H]QNB] is the concentration of [$^3$H]QNB in the binding assay, and K$_D$ is the K$_D$ of [$^3$H]QNB. The K$_D$ of [$^3$H]QNB for hM1 is 114 pM and for hM2 is 169 pM. Values are means ± SEM (n = 3) unless otherwise indicated.
[b]Th value is the average of two determinations.
[c]Ki value was not calculated for this compound.

Figure 3:
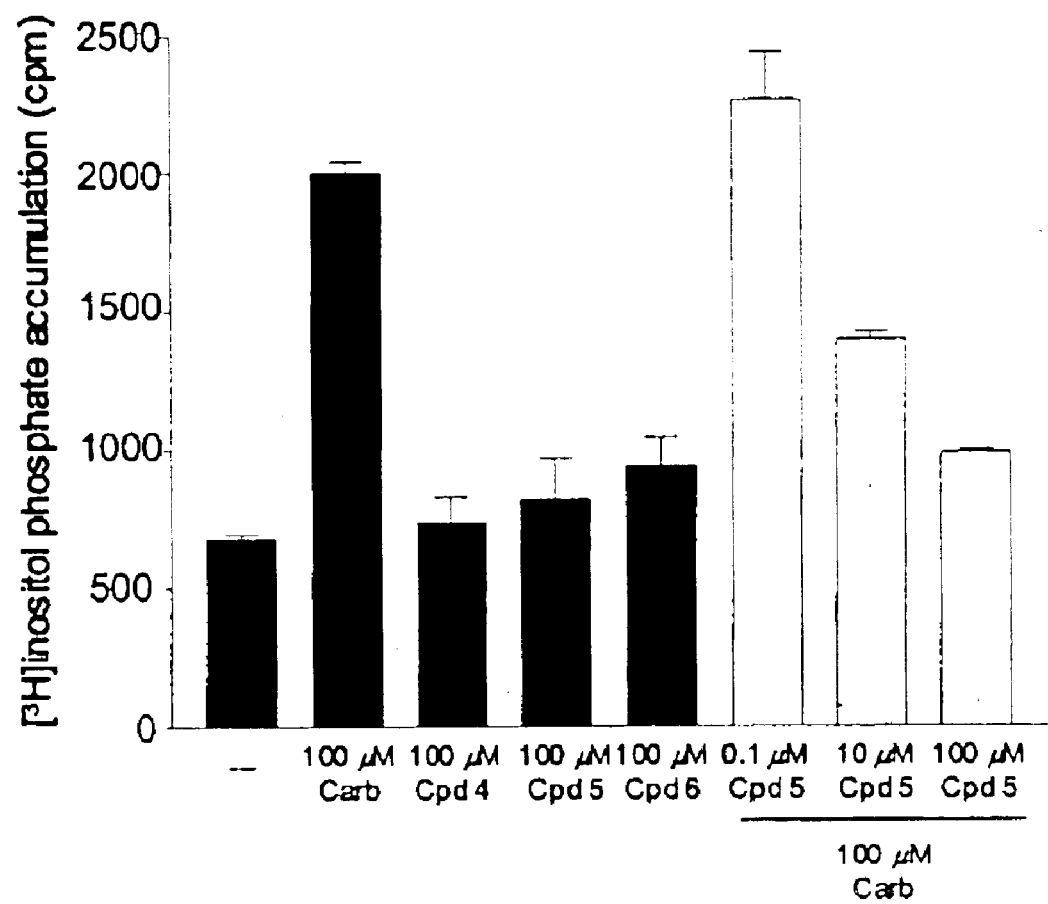
FIG. 3 demonstrates a functional activity assay at the human M1 receptor, wherein the accumulation of [$^3$H]inositol phosphates in Sf9 cells expressing the M1 muscarinic receptor was measured in response to 100 μM carbachol or compounds 4, 5, or 6 or with 100 μM carbachol with increasing amounts of compound 5.

A functional assay of M1 muscarinic receptors was performed. See FIG. 3. M1 receptor activity was determined by measuring activation of the Gα$_q$ effector, phospholipase C-β. Recombinant human M1 receptor was expressed (48 h) from a baculovirus in Sf9 insect cells. The inositol lipid pool of cells was radiolabeled by incubating the cells overnight in inositol-free Grace's medium containing 1 µCi of myo-[$^3$H]inositol. The medium was supplemented with 50 mM HEPES, pH 7.4, and 10 mM LiCl (final concentration) and placed in a 27° C. bath for 10 min prior to assay. The assay was initiated by addition of the appropriate ligand(s) and incubations continued for 20 min. The assay was terminated by aspirating the medium and adding 750 µL of ice-cold 50 mM formic acid. After 30 min at 4° C., the samples were neutralized with 250 µL of 150 mM NH$_4$OH. [$^3$H]Inositol phosphates were isolated by ion exchange chromatography on Dowex AG 1-X8 columns and quantitated by liquid scintillation counting. FIG. 3 demonstrates a functional activity of analogues at the human M1 receptor: The accumulation of [$^3$H]inositol phosphates in Sf9 cells expressing the M1 muscarinic receptor was measured in response to 100 µM carbachol (Carb) or compound 4, 5, or 6 or with 100 µM carbachol with increasing amounts of compound 5. The data shown in FIG. 3 are the results of an experiment performed in triplicate.

Figure 4:
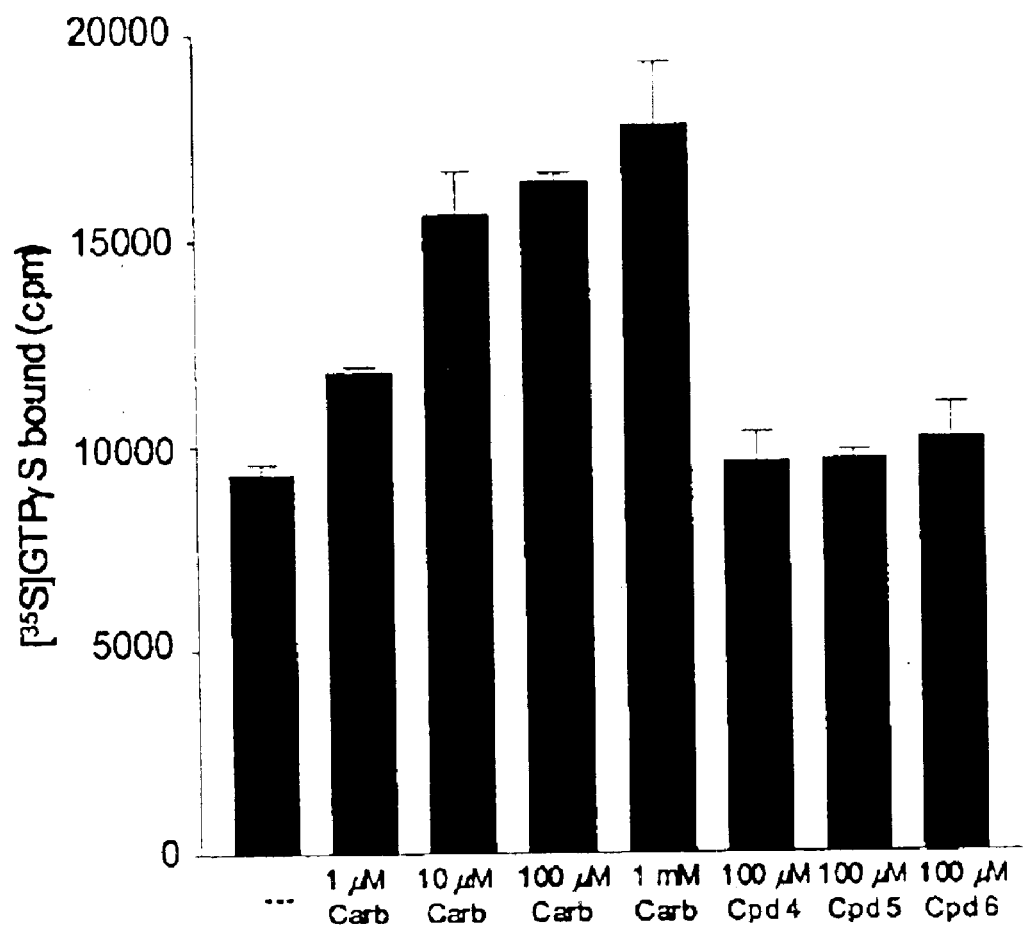
FIG. 4 shows a functional activity assay at the human M2 receptor, wherein [$^{35}$S]GTPγS binding assays were carried out in Sf9 cell membranes expressing the M2 muscarinic receptor in the presence of increasing concentrations of carbachol or 100 μM of compounds 4, 5, or 6.
Figure 5:
FIG. 5 shows the pharmacophore elements present in compounds 5, 6, 19 and 20.
Figure 5:
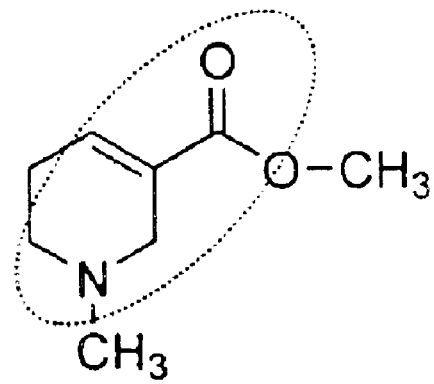
Figure 5:
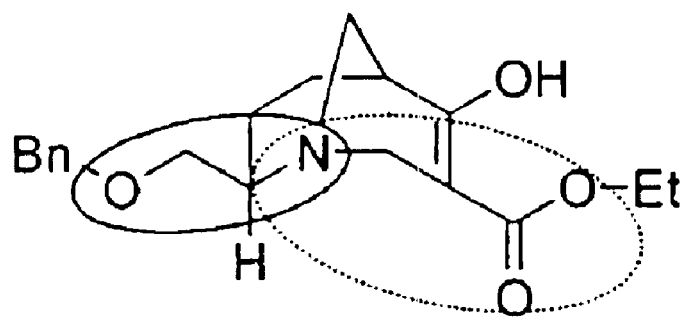
Figure 5:
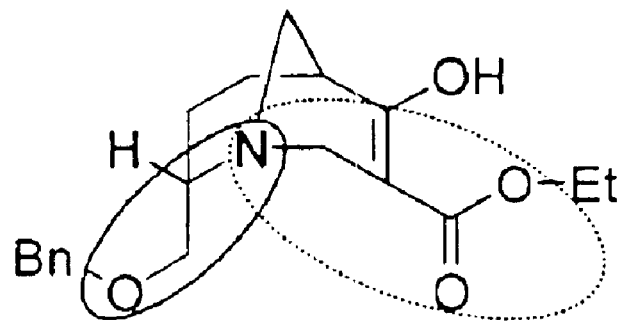

Additionally, a functional assay of M2 muscarinic receptors using the present compounds was undertaken as follows. Agonist activity at the M2 receptor was determined by measuring ligand-promoted [$^{35}$S]GTPγS binding. Recombinant human M2 receptor was expressed (48 h) from a baculovirus in Sf9 insect cells. Membranes prepared from these cells were treated with 8 M urea to remove all non-integral proteins from the membrane. The membranes were washed and resuspended in reconstitution buffer (25 mM Hepes, pH 7.4, 100 mM NaCl, 5 mM MgCl$_2$, 1 mM EDTA, 0.1% bovine serum albumin). A membrane suspension containing approximately 200 fmol of receptor was pre-incubated with 1 µM AMP-PNP for 15 min at 4° C. Purified Gα$_{i1}$ and β$_{1γ2}$ were added to a final concentration of 10 nM followed by the addition of concentrated GDP for a final concentration of 50 nM. This mix was incubated for 45 min at 4° C. The assay was initiated by the addition of the appropriate ligand followed by [$^{35}$S]GTPγS to a final concentration of approximately 7 nM and the incubation continued at 25° C. for 2 min. Membranes were collected by vacuum filtration using GF/A filters and radioactivity was quantitated by liquid scintillation counting. FIG. 4 illustrates the functional activity of analogues at the human M2 receptor: [$^{35}$S]GTPγS binding assays were carried out in Sf9 cell membranes expressing the M2 muscarinic receptor in the presence of increasing concentrations of carbachol (Carb) or 100 µM of compound 4, 5, or 6. The data shown in FIG. 4 are the result of an experiment performed in triplicate.

It was additionally observed that exo-8-benzyloxymethyl-3-ethoxycarbonyl-4-hydroxy-1-azabicyclo[3.3.1]non-3-ene (compound 5) functioned as a muscarinic receptor antagonist with a Ki only 14-fold greater than atropine at the human M2 receptor. It may be possible for these compounds to act as partial agonists or agonists at these receptors as well.

Figure 7:
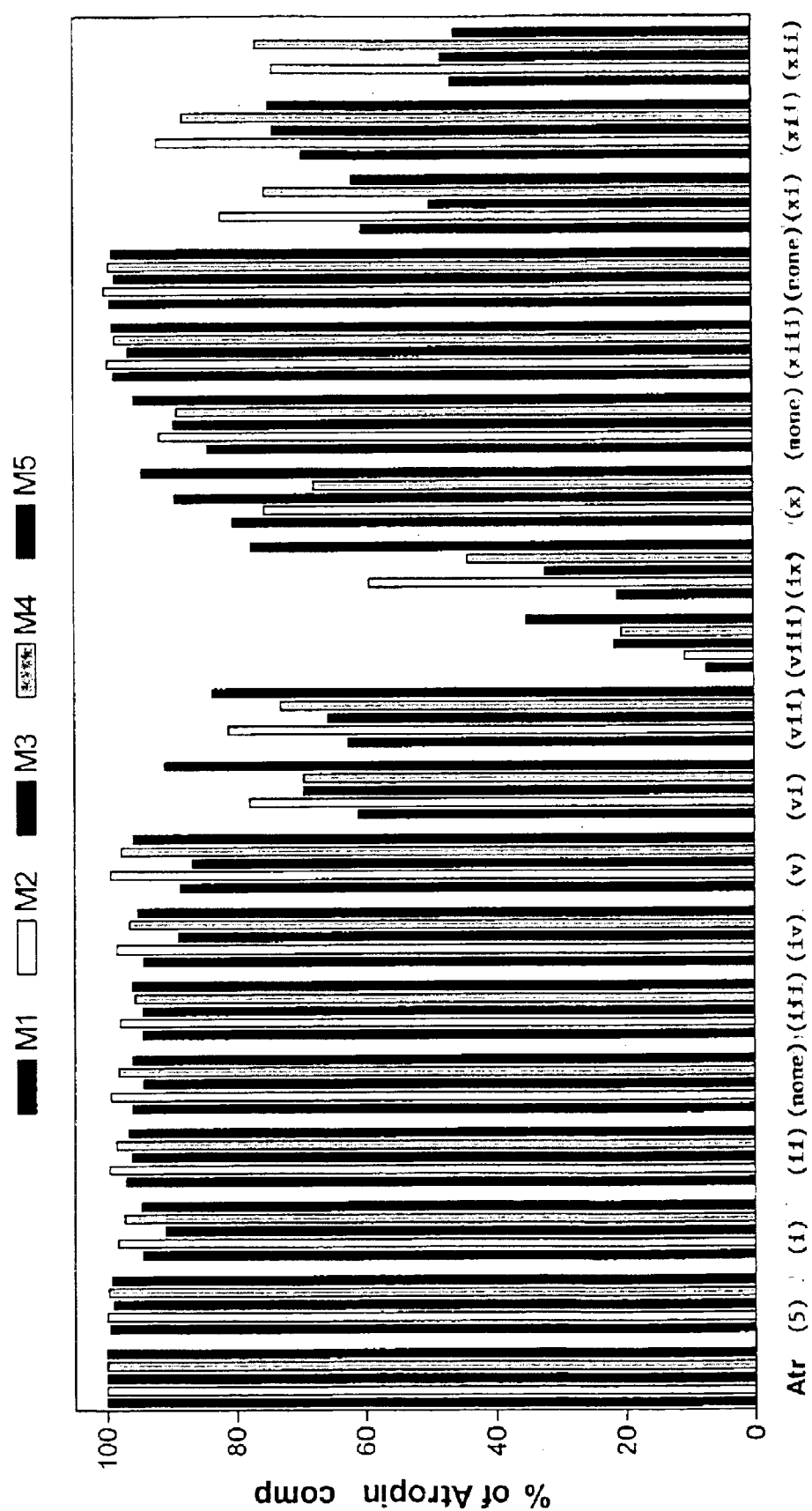
FIG. 7 illustrates a bar graph depicting a competitive binding assay at the $M_1$–$M_5$ receptors for atropine and some of the ligands of the present invention.

Muscarinic M1 through M5 Binding Assay. COS-7 cells were subcultured in 150 mm dishes to a density of 20,000 cells/cm$^2$. The cells were transfected with Fugene 6 transfection reagent (according to manufacturer's specifications) and pcDNA3.1 DNA containing sequence coding for hM1, hM2, hM3, hM4, or hM5 receptor (approximately 20 µg DNA/150 mm dish). Cell lysates were harvested after 24 hr by scraping the cells and sonicating in buffer (5 mM Tris pH 7.5, 1 mM MgCl$_2$, and protease inhibitors). Membranes were isolated by differential centrifugation and resuspended in freezing buffer (20 mM HEPES pH 8, 250 mM sucrose, 0.1 mM EDTA, and protease inhibitors). Binding assays were carried out as previously described. FIG. 7 depicts a competitive binding assay at the M$_1$–M$_5$ receptors for atropine and many of the ligands (100 µM) of the present invention as labeled.

The foregoing is illustrative of the present invention, and is not to be construed as limiting thereof. The invention is defined by the following claims, with equivalents of the claims to be included therein.

What is claimed is:

1. A compound of formula I

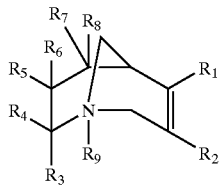

wherein $R_1$ is selected from the group consisting of hydroxy and alkoxy;

$R_2$ is selected from the group consisting of ketone, aldehyde, ester and carboxylic acid;

$R_3$ is selected from the group consisting of hydrogen, alkyloxyalkyl, alkylaminoalkyl, dialkylaminoalkyl and alkoxy unsubstituted or substituted;

$R_4$ is selected from the group consisting of hydrogen, alkyloxyalkyl, alkylaminoalkyl, dialkylaminoalkyl and alkoxy unsubstituted or substituted;

$R_5$ to $R_8$ are hydrogen;

$R_9$ is selected from the group consisting of hydrogen, alkyl and alkylaryl, unsubstituted or substituted; and wherein one and only one of $R_3$ and $R_4$ is hydrogen.

2. The compound of claim 1, wherein when the $R_4$ moiety is alkyloxyalkyl, alkylaminoalkyl, dialkylaminoalkyl and alkoxy, unsubstituted or substituted it exists as an exo isomer.

3. A compound selected from the group consisting of exo-8-benzyloxymethyl-3-ethoxycarbonyl-4-hydroxy-1-azabicyclo[3.3.1]non-3-ene, exo-8-Benzyloxymethyl-3-methoxycarbonyl-4-hydroxy-1-azabicyclo[3.3.1]non-3-ene, exo-8-Benzyloxymethyl-3-allyloxycarbonyl-4-hydroxy-1-azabicyclo[3.3.1]non-3-ene, exo-8-Benzyloxymethyl-3-hexyloxycarbonyl-4-hydroxy-1-azabicyclo[3.3.1]non-3-ene, exo-8-Benzyloxymethyl-3-ethoxycarbonyl-4-hydroxy-1-methyl-1-azabicyclo[3.3.1]non-3-ene iodide, exo-8-Benzyloxymethyl-3-ethoxycarbonyl-4-hydroxy-1-ethyl-1-azabicyclo[3.3.1]non-3-ene trifluoromethanesulfonate, exo-8-Hydroxymethyl-3-ethoxycarbonyl-4-hydroxy-1-azabicyclo[3.3.1]non-3-ene, exo-8-Acetoxymethyl-3-ethoxycarbonyl-4-hydroxy-1-azabicyclo[3.3.1]non-3-ene, exo-8-(2',2')-Diphenyl)propionoxymethyl-3-ethoxycarbonyl-4-hydroxy-1-azabicyclo[3.3.1]non-3-ene, exo-8-Ethylaminocarbonyloxymethyl-3-ethoxycarbonyl-4-hydroxy-1-azabicyclo[3.3.1]non-3-ene, exo-8-Phenylaminocarbonyloxymethyl-3-ethoxycarbonyl-4-hydroxy-1-azabicyclo[3.3.1]non-3-ene, and exo-8-Benzyloxymethyl-3-ethoxycarbonyl-4-methoxy-1-azabicyclo[3.3.1]non-3-ene.

4. A pharmaceutical composition comprising a compound group of formula I

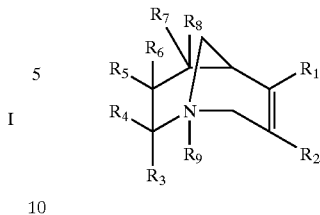

or an ester or pharmaceutically acceptable salt, solvate, hydrate, or combination thereof, in an amount effective for regulating central nervous system functions, and a pharmaceutically acceptable vehicle, wherein $R_1$ is selected from the group consisting of hydroxy and alkoxy;

$R_2$ is selected from the group consisting of ketone, aldehyde, ester and carboxylic acid, unsubstituted or substituted;

$R_3$ is selected from the group consisting of hydrogen, alkyloxyalkyl, alkylaminoalkyl, dialkylaminoalkyl and alkoxy unsubstituted or substituted;

$R_4$ is selected from the group consisting of hydrogen, alkyloxyalkyl, alkylaminoalkyl, dialkylaminoalkyl and alkoxy unsubstituted or substituted;

$R_5$ to $R_8$ are hydrogen;

$R_9$ is selected from the group consisting of hydrogen, alkyl and alkylaryl, unsubstituted or substituted;

wherein one and only one of $R_3$ and $R_4$ is hydrogen;

wherein said composition is administered in an amount sufficient to regulate a cholinergic receptor.

5. The pharmaceutical composition of claim 4, wherein said compound comprises of at least two pharmacophores.

6. The pharmaceutical composition of claim 4, wherein when the $R_4$ moiety is alkyloxyalkyl, alkylaminoalkyl, dialkylaminoalkyl and alkoxy unsubstituted or substituted it exists as an exo isomer.

7. The pharmaceutical composition of claim 4, wherein the cholinergic receptor is selected from the group consisting of nicotinic and muscarinic receptors.

8. A pharmaceutical composition comprising a compound selected from the group consisting of exo-8-benzyloxymethyl-3-ethoxycarbonyl-4-hydroxy-1-azabicyclo[3.3.1]non-3-ene, exo-8-Benzyloxymethyl-3-methoxycarbonyl-4-hydroxy-1-azabicyclo[3.3.1]non-3-ene, exo-8-Benzyloxymethyl-3-allyloxycarbonyl-4-hydroxy-1-azabicyclo[3.3.1]non-3-ene, exo-8-Benzyloxymethyl-3-hexyloxycarbonyl-4-hydroxy-1-azabicyclo[3.3.1]non-3-ene, exo-8-Benzyloxymethyl-3-ethoxycarbonyl-4-hydroxy-1-methyl-1-azabicyclo[3.3.1]non-3-ene iodide, exo-8-Benzyloxymethyl-3-ethoxycarbonyl-4-hydroxy-1-ethyl-1-azabicyclo[3.3.1]non-3-ene trifluoromethanesulfonate, exo-8-Hydroxymethyl-3-ethoxycarbonyl-4-hydroxy-1-azabicyclo[3.3.1]non-3-ene, exo-8-Acetoxymethyl-3-ethoxycarbonyl-4-hydroxy-1-azabicyclo[3.3.1]non-3-ene, exo-8-(2',2')-Diphenyl)propionoxymethyl-3-ethoxycarbonyl-4-hydroxy-1-azabicyclo[3.3.1]non-3-ene, exo-8-Ethylaminocarbonyloxymethyl-3-ethoxycarbonyl-4-hydroxy-1-azabicyclo[3.3.1]non-3-ene, exo-8-Phenylaminocarbonyloxymethyl-3-ethoxycarbonyl-4-hydroxy-1-azabicyclo[3.3.1]non-3-ene, and exo-8-Benzyloxymethyl-3-ethoxycarbonyl-4-methoxy-1-azabicyclo[3.3.1]non-3-ene; and a pharmaceutically acceptable carrier.

9. A method of treating a subject with a cognitive function disorder, a central nervous system disorder, an autonomic nervous system disorder, a bronchodilation disorder or a gastrointestinal function disorder comprising administering to the subject a therapeutically effective amount of a compound or pharmaceutically acceptable salt thereof of a compound of Formula I

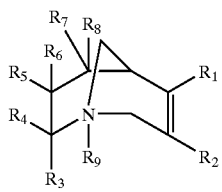

wherein $R_1$ is selected from the group consisting of hydroxy and alkoxy, unsubstituted or substituted;
$R_2$ is selected from the group consisting of ketone, aldehyde, ester and carboxylic acid, unsubstituted or substituted;
$R_3$ is selected from the group consisting of hydrogen, alkyloxyalkyl, alkylaminoalkyl, dialkylaminoalkyl and alkoxy unsubstituted or substituted;
$R_4$ is selected from the group consisting of hydrogen, alkyloxyalkyl, alkylaminoalkyl, dialkylaminoalkyl and alkoxy unsubstituted or substituted;
$R_5$ to $R_8$ are hydrogen;
$R_9$ is selected from the group consisting of hydrogen, alkyl and alkylaryl, unsubstituted or substituted; and
wherein one and only one of $R_3$ and $R_4$ is hydrogen.

10. The method according to claim 9, wherein said cognitive function disorder is Alzheimer's disease.

11. The method according to claim 9, wherein said central nervous system disorder is bronchodilation.

12. The method according to claim 9, wherein said gastrointestinal function disorder is selected from the group consisting of Crohn's disease and irritable bowel syndrome.

13. The method according to claim 9, wherein said compound comprises of at least two pharmacophores.

14. The method according to claim 9, wherein when the $R_4$ moiety is alkyloxyalkyl, alkylaminoalkyl, dialkylaminoalkyl and alkoxy, unsubstituted or substituted it exists as an exo isomer.

15. A compound of formula II

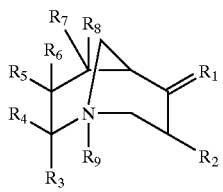

wherein
$R_1$ is selected from the group consisting of oxygen, and oxime, unsubstituted or substituted;
$R_2$ is hydrogen;
$R_3$ is selected from the group consisting of hydrogen, alkyloxyalkyl, alkylaminoalkyl, dialkylaminoalkyl and alkoxy unsubstituted or substituted;
$R_4$ is selected from the group consisting of hydrogen, alkyloxyalkyl, alkylaminoalkyl, dialkylaminoalkyl and alkoxy unsubstituted or substituted;

$R_5$ to $R_8$ are hydrogen;
$R_9$ is selected from the group consisting of hydrogen, alkyl and alkylaryl, unsubstituted or substituted; and
wherein one and only one of $R_3$ and $R_4$ is hydrogen.

16. The compound of claim 15, wherein when the $R_4$ moiety is alkyloxyalkyl, alkylaminoalkyl, dialkylaminoalkyl and alkoxy, unsubstituted or substituted it exists as an exo isomer.

17. A compound selected from the group consisting of exo-8-Benzyloxymethyl-1-azabicyclo[3.3.1]nonan-4-one, and exo-8-Benzyloxymethyl-1-azabicyclo[3.3.1]nonan-4-one, O-Methyloxime.

18. A pharmaceutical composition comprising a compound group of formula II

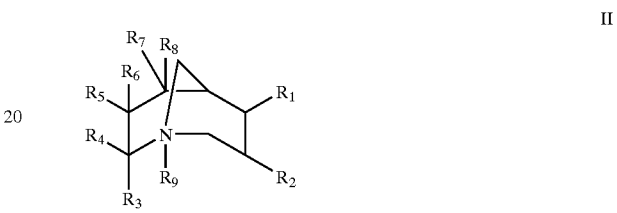

or an ester or pharmaceutically acceptable salt, solvate, hydrate, or combination thereof, in an amount effective for regulating central nervous system functions, and a pharmaceutically acceptable vehicle, wherein
$R_1$ is selected from the group consisting of oxygen, and oxime, unsubstituted or substituted;
$R_2$ is hydrogen;
$R_3$ is selected from the group consisting of hydrogen, alkyloxyalkyl, alkylaminoalkyl, dialkylaminoalkyl and alkoxy unsubstituted or substituted;
$R_4$ is selected from the group consisting of hydrogen, alkyloxyalkyl, alkylaminoalkyl, dialkylaminoalkyl and alkoxy unsubstituted or substituted;
$R_9$ is selected from the group consisting of hydrogen, alkyl and alkylaryl, unsubstituted or substituted;
$R_5$ to $R_8$ are hydrogen; and
wherein one and only one of $R_3$ and $R_4$ is hydrogen;
wherein said composition is administered in an amount sufficient to regulate a cholinergic receptor.

19. The pharmaceutical composition of claim 18, wherein said compound comprises of at least two pharmacophores.

20. The pharmaceutical composition of claim 18, wherein when the $R_4$ moiety is alkyloxyalkyl, alkylaminoalkyl, dialkylaminoalkyl and alkoxy, unsubstituted or substituted it exists as an exo isomer.

21. The pharmaceutical composition of claim 18, wherein the cholinergic receptor is selected from the group consisting of nicotinic and muscarinic receptors.

22. A pharmaceutical composition comprising a compound selected from the group consisting of exo-8-Benzyloxymethyl-1-azabicyclo[3.3.1]nonan-4-one, and exo-8-Benzyloxymethyl-1-azabicyclo[3.3.1]nonan-4-one, O-Methyloxime; and
a pharmaceutically acceptable carrier.

23. A method of treating a subject with a cognitive function disorder, a central nervous system disorder, an autonomic nervous system disorder, a bronchodilation disorder or a gastrointestinal function disorder comprising administering to the subject a therapeutically effective amount of a compound or pharmaceutically acceptable salt thereof of a compound of Formula II

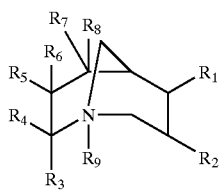

wherein $R_1$ is selected from the group consisting of oxygen, and oxime, unsubstituted or substituted;

$R_2$ is hydrogen;

$R_3$ is selected from the group consisting of hydrogen, alkyloxyalkyl, alkylaminoalkyl, dialkylaminoalkyl and alkoxy unsubstituted or substituted;

$R_4$ is selected from the group consisting of hydrogen, alkyloxyalkyl, alkylaminoalkyl, dialkylaminoalkyl and alkoxy unsubstituted or substituted;

$R_5$ to $R_8$ are hydrogen;

$R_9$ is selected from the group consisting of hydrogen, alkyl and alkylaryl, unsubstituted or substituted; and wherein one and only one of $R_3$ and $R_4$ is hydrogen.

24. The method according to claim 23, wherein said cognitive function disorder is Alzheimer's disease.

25. The method according to claim 23, wherein said central nervous system disorder is bronchodilation.

26. The method according to claim 23, wherein said gastrointestinal function disorder is selected from the group consisting of Crohn's disease and irritable bowel syndrome.

27. The method according to claim 23, wherein said compound comprises of at least two pharmacophores.

28. The method according to claim 23, wherein when the $R_4$ moiety is alkyloxyalkyl, alkylaminoalkyl, dialkylaminoalkyl and alkoxy, unsubstituted or substituted it exists as an exo isomer.

* * * * *

UNITED STATES PATENT AND TRADEMARK OFFICE
CERTIFICATE OF CORRECTION

PATENT NO. : 6,875,774 B2
DATED : April 5, 2005
INVENTOR(S) : Kohn et al.

Page 1 of 1

It is certified that error appears in the above-identified patent and that said Letters Patent is hereby corrected as shown below:

Column 29,
Line 20, should read -- $R_1$ is selected from the group consisting of hydroxy and alkoxy, unsubstituted or substituted; --.

Column 30,
Line 17, should read -- $R_1$ is selected from the group consisting of hydroxy and alkoxy, unsubstituted or substituted; --.
Line 32, should read -- wherein one and only one of $R_3$ and $R_4$ is hydrogen; and --.

Column 31,
Lines 21-22, should read -- aldehyde, ester and carboxylic acid; --.

Column 32,
Lines 39-45 should read -- $R_5$ to $R_8$ are hydrogen;
$R_9$ is selected from the group consisting of hydrogen, alkyl and alkylaryl, unsubstituted or substituted; and wherein one and only one of $R_3$ and $R_4$ is hydrogen. --.

Signed and Sealed this

Twentieth Day of September, 2005

JON W. DUDAS
*Director of the United States Patent and Trademark Office*